US012582608B2

(12) United States Patent
Kanasty et al.

(10) Patent No.: US 12,582,608 B2
(45) Date of Patent: Mar. 24, 2026

(54) COATINGS FOR GASTRIC RESIDENCE DOSAGE FORMS

(71) Applicant: Nortiva Bio, Inc., Lexington, MA (US)

(72) Inventors: Rosemary Kanasty, Cambridge, MA (US); Tyler Grant, Arlington, MA (US); Erick Peeke, Cambridge, MA (US); Nupura Bhise, Watertown, MA (US); David Altreuter, Watertown, MA (US); Sonia Holar, Watertown, MA (US); Marlene Schwarz, Watertown, MA (US)

(73) Assignee: NORTIVA BIO, INC., Lexington, MA (US)

( * ) Notice: Subject to any disclaimer, the term of this patent is extended or adjusted under 35 U.S.C. 154(b) by 896 days.

(21) Appl. No.: 17/593,437

(22) PCT Filed: Mar. 19, 2020

(86) PCT No.: PCT/US2020/023710
§ 371 (c)(1),
(2) Date: Sep. 17, 2021

(87) PCT Pub. No.: WO2020/191231
PCT Pub. Date: Sep. 24, 2020

(65) Prior Publication Data
US 2022/0192995 A1    Jun. 23, 2022

Related U.S. Application Data

(60) Provisional application No. 62/821,361, filed on Mar. 20, 2019.

(51) Int. Cl.
*A61K 9/48* (2006.01)
*A61K 45/06* (2006.01)

(52) U.S. Cl.
CPC .......... *A61K 9/4891* (2013.01); *A61K 9/4833* (2013.01); *A61K 9/485* (2013.01); *A61K 9/4858* (2013.01); *A61K 9/4866* (2013.01); *A61K 45/06* (2013.01)

(58) Field of Classification Search
CPC .... A61K 9/4891; A61K 9/4833; A61K 9/485; A61K 9/4858; A61K 9/4866; A61K 45/06
See application file for complete search history.

(56) References Cited

U.S. PATENT DOCUMENTS

| | | | |
|---|---|---|---|
| 6,200,603 | B1 | 3/2001 | Rowe et al. |
| 9,737,905 | B2 | 8/2017 | Byron et al. |
| 9,827,203 | B2 | 11/2017 | Stella et al. |
| 10,182,985 | B2 | 1/2019 | Bellinger et al. |
| 10,413,507 | B2 | 9/2019 | Zhang et al. |
| 10,517,819 | B2 | 12/2019 | Bellinger et al. |
| 10,517,820 | B2 | 12/2019 | Bellinger |
| 10,532,027 | B2 | 1/2020 | Bellinger |
| 10,596,110 | B2 | 3/2020 | Bellinger |
| 10,610,482 | B2 | 4/2020 | Bellinger |
| 10,716,751 | B2 | 7/2020 | Bellinger et al. |
| 10,716,752 | B2 | 7/2020 | Bellinger et al. |
| 10,849,853 | B2 | 12/2020 | Bellinger et al. |
| 10,953,208 | B2 | 3/2021 | Zhang et al. |
| 11,077,056 | B2 | 8/2021 | Bellinger et al. |
| 11,083,690 | B2 | 8/2021 | Zhang et al. |
| 11,246,829 | B2 | 2/2022 | Bellinger et al. |
| 11,357,723 | B2 | 6/2022 | Bellinger et al. |
| 11,389,399 | B2 | 7/2022 | Bellinger et al. |
| 11,576,859 | B2 | 2/2023 | Kanasty et al. |
| 11,576,866 | B2 | 2/2023 | Bellinger et al. |
| 11,793,751 | B2 | 10/2023 | Grant et al. |
| 11,992,552 | B2 | 5/2024 | Bellinger |
| 12,023,406 | B2 | 7/2024 | Kanasty |
| 12,109,305 | B2 | 10/2024 | Bellinger |
| 12,142,158 | B2 | 11/2024 | Kanasty |
| 2005/0064027 | A1 | 3/2005 | Jacob et al. |
| 2006/0257484 | A1 | 11/2006 | Hwang et al. |
| 2008/0206145 | A1 | 8/2008 | Afargan |
| 2009/0304768 | A1 | 12/2009 | Lapidot et al. |
| 2010/0064100 | A1 | 3/2010 | Bains |
| 2011/0091542 | A1 | 4/2011 | Navon et al. |

(Continued)

FOREIGN PATENT DOCUMENTS

| | | |
|---|---|---|
| CN | 102300463 A | 12/2011 |
| JP | 2006508021 A | 3/2006 |

(Continued)

OTHER PUBLICATIONS

Extended European Search Report, dated Dec. 13, 2022, for European Patent Application No. 20773419.5, 9 pages.
Li, H. et al. (2006). Coated Pharmaceutical Dosage Forms, China Pharmaceutical Science and Technology Press, pp. 109-111. [English Translation: Bauer, K.H. et al. (1998). "Biopharmaceutical Aspects," Chapter 5 in Coated Pharmaceutical Dosage Forms: Fundamentals, Manufacturing Techniques, Biopharmaceutical Aspects, Test Methods, and Raw Materials, CRC Press: Boca Raton, 23 pages.].
Partial Supplementary Search Reports, dated Mar. 29, 2023, for European Patent Application No. 20774505.0, 12 pages.
International Preliminary Report on Patentability, issued Sep. 16, 2021, for PCT Application No. PCT/US2020/023704, filed Mar. 19, 2020, 8 pages.
International Search Report and Written Opinion, mailed Jun. 3, 2020, for PCT Application No. PCT/US2020/0023710, filed Mar. 19, 2020, 10 pages.

(Continued)

*Primary Examiner* — Michael P Cohen
(74) *Attorney, Agent, or Firm* — MORRISON & FOERSTER LLP

(57) ABSTRACT

Provided are enrobed gastric residence dosage forms comprising: a gastric residence system in a folded configuration; and a coating enrobing the gastric residence system in the folded configuration, wherein the enrobed gastric residence dosage form is configured to release the gastric residence system in the folded configuration in a stomach of a patient, allowing the gastric residence system to assume an open configuration. The coating comprises water, a plasticizer, a gelling agent, and/or a polymer.

18 Claims, 15 Drawing Sheets

(56) References Cited

U.S. PATENT DOCUMENTS

| | | | |
|---|---|---|---|
| 2015/0366815 A1* | 12/2015 | Teles | A61K 9/4825 |
| | | | 514/769 |
| 2016/0317796 A1 | 11/2016 | Zhang et al. | |
| 2017/0106099 A1 | 4/2017 | Bellinger | |
| 2017/0128576 A1 | 5/2017 | Zhang et al. | |
| 2017/0135954 A1 | 5/2017 | Bellinger et al. | |
| 2017/0266112 A1 | 9/2017 | Bellinger et al. | |
| 2018/0311154 A1 | 11/2018 | Bellinger et al. | |
| 2019/0000768 A1 | 1/2019 | Shimokawa | |
| 2019/0070107 A1 | 3/2019 | Bellinger et al. | |
| 2019/0070108 A1 | 3/2019 | Bellinger et al. | |
| 2019/0070143 A1 | 3/2019 | Boulas et al. | |
| 2019/0125667 A1 | 5/2019 | Bellinger et al. | |
| 2019/0133936 A1 | 5/2019 | Bellinger et al. | |
| 2019/0175500 A1 | 6/2019 | Bellinger et al. | |
| 2019/0231697 A1 | 8/2019 | Bellinger et al. | |
| 2019/0254966 A1 | 8/2019 | Bellinger et al. | |
| 2019/0262265 A1 | 8/2019 | Bellinger et al. | |
| 2019/0298652 A1 | 10/2019 | Bellinger et al. | |
| 2020/0030234 A1 | 1/2020 | Zhang et al. | |
| 2020/0085736 A1 | 3/2020 | Bellinger et al. | |
| 2020/0085737 A1 | 3/2020 | Bellinger et al. | |
| 2020/0146979 A1 | 5/2020 | Kanasty | |
| 2020/0281851 A1 | 9/2020 | Grant et al. | |
| 2021/0093564 A1 | 4/2021 | Bellinger et al. | |
| 2021/0113460 A1 | 4/2021 | Bellinger et al. | |
| 2021/0128460 A1 | 5/2021 | Bellinger et al. | |
| 2021/0177750 A1 | 6/2021 | Bellinger et al. | |
| 2021/0196627 A1 | 7/2021 | Grant et al. | |
| 2022/0093006 A1 | 3/2022 | Kanasty et al. | |
| 2022/0160642 A1 | 5/2022 | Bhise et al. | |
| 2022/0387310 A1 | 12/2022 | Altreuter et al. | |
| 2022/0387311 A1 | 12/2022 | Kanasty et al. | |
| 2022/0387312 A1 | 12/2022 | Kanasty et al. | |
| 2022/0409528 A1 | 12/2022 | Kanasty et al. | |
| 2023/0039421 A1 | 2/2023 | Bellinger et al. | |
| 2023/0190941 A1 | 6/2023 | Montezco et al. | |
| 2024/0139102 A1 | 5/2024 | Grant | |
| 2024/0252483 A1 | 8/2024 | Bhise | |
| 2024/0335400 A1 | 10/2024 | Beguin | |
| 2024/0342081 A1 | 10/2024 | Bellinger | |
| 2024/0382418 A1 | 11/2024 | Kanasty | |
| 2024/0390270 A1 | 11/2024 | Kanasty | |
| 2024/0398701 A1 | 12/2024 | Kanasty | |
| 2024/0423909 A1 | 12/2024 | Bellinger | |

FOREIGN PATENT DOCUMENTS

| | | |
|---|---|---|
| JP | 2007145756 A | 6/2007 |
| JP | 2009523175 A | 6/2009 |
| JP | 2012500230 A | 1/2012 |
| JP | 2012510987 A | 5/2012 |
| JP | 2013129669 A | 7/2013 |
| JP | 2017518308 A | 7/2017 |
| JP | 2017524662 A | 8/2017 |
| JP | 2018517735 A | 7/2018 |
| WO | 2003082204 A2 | 10/2003 |
| WO | 2007002518 A1 | 1/2007 |
| WO | 2007083309 A2 | 7/2007 |
| WO | 2007084818 A2 | 7/2007 |
| WO | 2010064100 A1 | 6/2010 |
| WO | 2010064139 A2 | 6/2010 |
| WO | 2010128495 A1 | 11/2010 |
| WO | 2011048494 A2 | 4/2011 |
| WO | 2015187746 A1 | 12/2015 |
| WO | 2015191920 A1 | 12/2015 |
| WO | 2015191922 A1 | 12/2015 |
| WO | 2015191925 A1 | 12/2015 |
| WO | 2016178971 A1 | 11/2016 |
| WO | 2016205270 A1 | 12/2016 |
| WO | 2017022248 A1 | 2/2017 |
| WO | 2017070612 A1 | 4/2017 |
| WO | 2017100367 A1 | 6/2017 |
| WO | 2017205844 A2 | 11/2017 |
| WO | 2017205844 A3 | 1/2018 |
| WO | 2018064630 A1 | 4/2018 |
| WO | 2018102799 A1 | 6/2018 |
| WO | 2018227147 A1 | 12/2018 |
| WO | 2019060458 A1 | 3/2019 |
| WO | 2020036972 A1 | 2/2020 |
| WO | 2020117855 A1 | 6/2020 |
| WO | 2020191229 A1 | 9/2020 |
| WO | 2020191231 A1 | 9/2020 |
| WO | 2021092483 A1 | 5/2021 |
| WO | 2021092484 A1 | 5/2021 |
| WO | 2021092486 A1 | 5/2021 |
| WO | 2021092487 A1 | 5/2021 |
| WO | 2021092491 A1 | 5/2021 |
| WO | 2022159529 A1 | 7/2022 |
| WO | 2022236288 A1 | 11/2022 |
| WO | 2022236289 A1 | 11/2022 |
| WO | 2023141524 A2 | 7/2023 |
| WO | 2024031023 A2 | 2/2024 |
| WO | 2024073752 A2 | 4/2024 |
| WO | 2024249946 A2 | 12/2024 |

OTHER PUBLICATIONS

International Preliminary Report on Patentability, issued Sep. 16, 2021, for PCT Application No. PCT/US2020/0023710, filed Mar. 19, 2020, 7 pages.

International Search Report and Written Opinion, mailed May 27, 2020, for PCT Application No. PCT/US2020/023704, iled Mar. 19, 2020, 11 pages.

Hu, Y. (Feb. 28, 2013). Pharmaceutical Formulations 2nd Edition, China Medical Science and Technology Press: Bejing, pp. 172-173, 15 pages. [English Machine Translation].

* cited by examiner

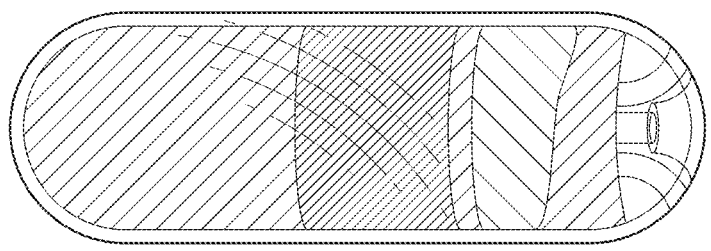
FIG. 6A
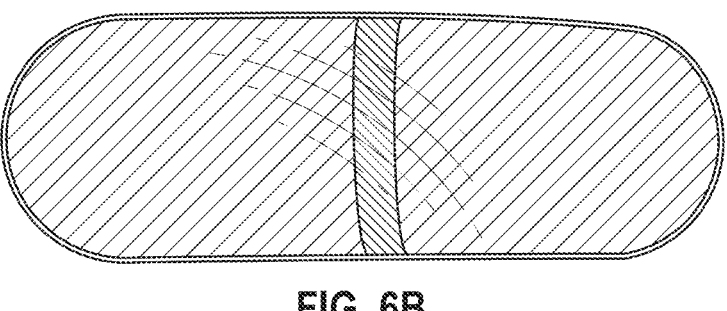
FIG. 6B
FIG. 6C

COATINGS FOR GASTRIC RESIDENCE DOSAGE FORMS

CROSS REFERENCE TO RELATED APPLICATIONS

This application is a national stage application under 35 U.S.C. § 371 of International Application No. PCT/US2020/023710, filed internationally on Mar. 19, 2020, which claims priority benefit of U.S. Provisional Patent Application No. 62/821,361 filed Mar. 20, 2019. The entire contents of that application are hereby incorporated by reference herein.

FIELD OF THE INVENTION

This relates to coatings, and more particularly, to coatings for gastric residence systems and gastric residence dosage forms.

BACKGROUND OF THE INVENTION

Gastric residence systems are delivery systems for therapeutic agents that can remain in the stomach for days to weeks, or even over longer periods, during which time the therapeutic agent can elute from the gastric residence system for absorption in the gastrointestinal tract. Gastric residence systems are typically designed to be administered to the stomach of a patient in a capsule. The encapsulated gastric residence system is swallowed or introduced into the stomach by an alternate method of administration (e.g., feeding tube or gastric tube). Upon dissolution of the capsule in the stomach, the gastric residence system expands or unfolds to a size which remains in the stomach and resists passage through the pyloric valve over the desired residence period (such as three days, seven days, two weeks, etc.). Once the desired residence time expires, the expanded or unfolded drug delivery device breaks into several smaller pieces which pass through the pyloric valve and are expelled from the patient.

SUMMARY OF THE INVENTION

Provided are coatings for gastric residence systems. Also provided are methods of preparing enrobed gastric residence dosage forms using the coatings for gastric residence systems. In particular, coatings described herein can help ensure that a gastric residence system of an enrobed gastric residence dosage form unfolds at a predetermined time and location within the gastrointestinal tract (i.e., in the stomach). For example, coatings provided herein can minimize the risk of the gastric residence system deploying too early (e.g., in the esophagus) and causing an obstruction. Coatings described herein may also minimize the possibility of the gastric residence system passing through the stomach and expanding or unfolding later in the gastrointestinal tract (i.e., intestine) and causing an obstruction. Further, coatings provided herein minimize the risk of a gastric residence dosage form passing through the gastrointestinal tract without unfolding at all. In each of these possible scenarios, the therapeutic agent is not delivered to the patient as intended.

As described above, gastric residence systems are typically designed to be administered to a patient in a capsule. The capsule may be transported to the stomach by swallowing, by feeding tube, by gastric tube, etc. However, coatings, and particularly coatings providing a hermetic seal, provide the benefit of being tamper-proof, unlike capsules. Thus, a gastric residence system enrobed in a coating to form an enrobed gastric residence dosage form can prevent a patient (or another person) from tampering with the gastric residence system.

Enrobed gastric residence dosage forms provided herein may include a sleeve or band to bind the gastric residence system in a collapsed or folded configuration. In some embodiments, a bound gastric residence system may be enrobed with a coating to form an enrobed gastric residence dosage form.

Similarly, methods for preparing an enrobed gastric residence dosage form as provided herein can include binding a folded gastric residence system with a sleeve. In some embodiments, methods can include enrobing the bound gastric residence system with a coating to form an enrobed gastric residence dosage form. In some embodiments, methods for preparing a gastric residence dosage form may also include coating the enrobed gastric residence dosage form with a reverse-enteric coating to encourage dissolution of the enrobed coating and release of the gastric residence system within the stomach of a patient.

In some embodiments, an enrobed gastric residence dosage form is provided, the enrobed gastric residence dosage form comprising: a gastric residence system in a folded configuration; and a coating enrobing the gastric residence system in the folded configuration, wherein the enrobed gastric residence dosage form is configured to release the gastric residence system in a stomach of a patient, allowing the gastric residence system to assume an open configuration.

In some embodiments of the enrobed gastric residence dosage form, a thickness of the coating enrobing the gastric residence system in the folded configuration is from 50 to 250 microns.

In some embodiments of the enrobed gastric residence dosage form, the coating enrobing the gastric residence system in the folded configuration is applied to the gastric residence system in the folded configuration using a rotary die encapsulation process.

In some embodiments of the enrobed gastric residence dosage form, the coating enrobing the gastric residence system in the folded configuration comprises a softgel type shell material.

In some embodiments of the enrobed gastric residence dosage form, the coating enrobing the gastric residence system in the folded configuration provides a hermetic seal.

In some embodiments of the enrobed gastric residence dosage form, the coating enrobing the gastric residence system in the folded configuration comprises water, a plasticizer, and a gelling agent.

In some embodiments of the enrobed gastric residence dosage form, the coating enrobing the gastric residence system in the folded configuration comprises from 5 to 10 wt. % water.

In some embodiments of the enrobed gastric residence dosage form, the plasticizer comprises one or more of glycerin or sorbitol.

In some embodiments of the enrobed gastric residence dosage form, the coating enrobing the gastric residence system in the folded configuration comprises from 20 to 60 wt. % plasticizer.

In some embodiments of the enrobed gastric residence dosage form, the gelling agent is one or more of gelatin, pullulan, hydroxypropyl methylcellulose, or potato starch.

In some embodiments of the enrobed gastric residence dosage form, the coating enrobing the gastric residence system in the folded configuration comprises from 35 to 75 wt. % gelling agent.

In some embodiments of the enrobed gastric residence dosage form, the coating enrobing the gastric residence system in the folded configuration comprises a polymer.

In some embodiments of the enrobed gastric residence dosage form, the polymer comprises a polymethacrylate-based polymer.

In some embodiments of the enrobed gastric residence dosage form, the coating enrobing the gastric residence system in the folded configuration comprises from 10 to 50 wt. % polymer.

In some embodiments of the enrobed gastric residence dosage form, the enrobed gastric residence dosage from comprises a sleeve, wherein the sleeve surrounds at least a portion of the gastric residence system in the folded configuration.

In some embodiments of the enrobed gastric residence dosage form, the sleeve comprises at least one of gelatin, hydroxypropyl methylcellulose, or pullulan.

In some embodiments of the enrobed gastric residence dosage form, the enrobed gastric residence dosage form comprises a capsule encapsulating the gastric residence system in the folded configuration.

In some embodiments of the enrobed gastric residence dosage form, the capsule comprises at least one of gelatin, hydroxypropyl methylcellulose, or pullulan.

In some embodiments of the enrobed gastric residence dosage form, the enrobed gastric residence dosage form comprises a coating on the coating enrobing the gastric residence system in the folded configuration.

In some embodiments of the enrobed gastric residence dosage form, the coating on the coating enrobing the gastric residence system comprises a reverse-enteric polymer.

In some embodiments of the enrobed gastric residence dosage form, the reverse-enteric polymer comprises a polymethacrylate-based polymer.

In some embodiments of the enrobed gastric residence dosage form, the coating on the coating enrobing the gastric residence system comprises an anti-tacking agent.

In some embodiments of the enrobed gastric residence dosage form, the anti-tacking agent comprises at least one of talc or magnesium stearate.

In some embodiments of the enrobed gastric residence dosage form, the coating on the coating enrobing the gastric residence system comprises a plasticizer.

In some embodiments of the enrobed gastric residence dosage form, the plasticizer comprises at least one of a phthalate, a phosphate, a citrate, a tartrate, an adipate, a sebacate, a sulfonamide, a succinate, a glycolate, a glycerolate, a benzoate, a myristate, a halogenated phenyl, or a poloxamer.

In some embodiments of the enrobed gastric residence dosage form, the plasticizer comprises at least one of triacetin or dibutyl sebacate.

In some embodiments of the enrobed gastric residence dosage form, the coating on the coating enrobing the gastric residence system comprises a hydration aid.

In some embodiments of the enrobed gastric residence dosage form, the hydration aid comprises at least one of a polyvinylpyrrolidone, a vinylpyrrolidone-vinyl acetate copolymer, a polyethylene glycol, mannitol, or hydroxypropyl methylcellulose.

In some embodiments of the enrobed gastric residence dosage form, the enrobed gastric residence dosage form allows the gastric residence system in the folded configuration to assume an open configuration in at least 20 minutes when exposed to an aqueous pH 7.0 environment.

In some embodiments of the enrobed gastric residence dosage form, the enrobed gastric residence dosage form allows the gastric residence system in the folded configuration to assume an open configuration in at least 30 minutes when exposed to an aqueous pH 7.0 environment.

In some embodiments of the enrobed gastric residence dosage form, the enrobed gastric residence dosage form allows the gastric residence system in the folded configuration to assume an open configuration in less than 20 minutes when exposed to an aqueous pH 3.0 environment.

In some embodiments of the enrobed gastric residence dosage form, the enrobed gastric residence dosage form allows the gastric residence system in the folded configuration to assume an open configuration in less than 15 minutes when exposed to an aqueous pH 3.0 environment.

In some embodiments of the enrobed gastric residence dosage form, the enrobed gastric residence dosage form is used to treat a patient.

In some embodiments of the enrobed gastric residence dosage form, the patient is a human.

In some embodiments, a coating for enrobing a gastric residence system is provided, the coating comprising: 5-10 wt. % water; 20-60 wt % plasticizer; and 35-75 wt. % gelling agent.

In some embodiments of the coating, the coating is configured to enrobe a gastric residence system in a folded configuration to form an enrobed gastric residence dosage form, and the enrobed gastric residence dosage form is configured to release the gastric residence system in the folded configuration in a stomach of a patient, allowing the gastric residence system in the folded configuration to assume an open configuration.

In some embodiments of the coating, a thickness of the coating of the enrobed gastric residence dosage form is from 50 to 250 microns.

In some embodiments of the coating, the coating of the enrobed gastric residence dosage form is applied to the gastric residence system in the folded configuration using a rotary die encapsulation process.

In some embodiments of the coating, the coating of the enrobed gastric residence dosage form comprises a softgel type shell material.

In some embodiments of the coating, the coating of the enrobed gastric residence dosage form provides a hermetic seal.

In some embodiments of the coating, the enrobed gastric residence dosage form allows the gastric residence system in the folded configuration to assume the open configuration in at least 20 minutes when exposed to an aqueous pH 7.0 environment.

In some embodiments of the coating, the enrobed gastric residence dosage form allows the gastric residence system in the folded configuration to assume the open configuration in at least 30 minutes when exposed to an aqueous pH 7.0 environment.

In some embodiments of the coating, the enrobed gastric residence dosage form allows the gastric residence system in the folded configuration to assume the open configuration in less than 20 minutes when exposed to an aqueous pH 3.0 environment.

In some embodiments of the coating, the enrobed gastric residence dosage form allows the gastric residence system in the folded configuration to assume the open configuration in less than 15 minutes when exposed to an aqueous pH 3.0 environment.

In some embodiments of the coating, the plasticizer comprises at least one of glycerin or sorbitol.

In some embodiments of the coating, the gelling agent is one or more of gelatin, pullulan, hydroxypropyl methylcellulose, or potato starch.

In some embodiments of the coating, the coating comprises a polymer.

In some embodiments of the coating, the polymer comprises a polymethacrylate-based polymer.

In some embodiments of the coating, the coating comprises from 10 to 50 wt. % polymer.

In some embodiments, an enrobed gastric residence dosage form comprising the coating for enrobing a gastric residence system of any embodiments provided herein is provided, wherein the enrobed gastric residence dosage form is used to treat a patient.

In some embodiments of the enrobed gastric residence dosage form, the patient is a human.

In some embodiments, a method of making an enrobed gastric residence dosage form is provided, the method comprising: enrobing a gastric residence system in a folded configuration with a coating to form an enrobed gastric residence dosage form.

In some embodiments of the method, the enrobed gastric residence dosage form is configured to release the gastric residence system in the folded configuration in a stomach of a patient, allowing the gastric residence system in the folded configuration to assume an open configuration.

In some embodiments of the method, a thickness of the coating on the enrobed gastric residence dosage form is from 50 to 250 microns.

In some embodiments of the method, enrobing a gastric residence system in a folded configuration with a coating to form an enrobed gastric residence dosage form comprises a rotary die encapsulation process.

In some embodiments of the method, the coating comprises a softgel type shell material.

In some embodiments of the method, the coating provides a hermetic seal.

In some embodiments of the method, the method comprises binding the gastric residence system in the folded configuration with a sleeve prior to enrobing.

In some embodiments of the method, the sleeve comprises at least one of gelatin, hydroxypropyl methylcellulose, or pullulan.

In some embodiments of the method, the method comprises encapsulating the gastric residence system in the folded configuration with a capsule prior to enrobing.

In some embodiments of the method, the capsule comprises at least one of gelatin, hydroxypropyl methylcellulose, or pullulan.

In some embodiments of the method, the coating comprises water, a plasticizer, and a gelling agent.

In some embodiments of the method, the coating comprises from 5 to 10 wt. % water.

In some embodiments of the method, the plasticizer comprises one or more of glycerin or sorbitol.

In some embodiments of the method, the coating comprises from 20 to 60 wt. % plasticizer.

In some embodiments of the method, the gelling agent is one or more of gelatin, pullulan, hydroxypropyl methylcellulose, or potato starch.

In some embodiments of the method, the coating comprises from 35 to 75 wt. % gelling agent.

In some embodiments of the method, the coating comprises a polymer.

In some embodiments of the method, the polymer comprises a polymethacrylate-based polymer.

In some embodiments of the method, the coating comprises from 10 to 50 wt. % polymer.

In some embodiments of the method, the method comprises coating the enrobed gastric residence dosage form with a reverse-enteric coating.

In some embodiments of the method, the reverse-enteric coating comprises a reverse-enteric polymer, an anti-tacking agent, and a plasticizer.

In some embodiments of the method, the anti-tacking agent comprises at least one of talc or magnesium stearate.

In some embodiments of the method, the plasticizer comprises at least one of a phthalate, a phosphate, a citrate, a tartrate, an adipate, a sebacate, a sulfonamide, a succinate, a glycolate, a glycerolate, a benzoate, a myristate, a halogenated phenyl, or a poloxamer.

In some embodiments of the method, the plasticizer comprises at least one of triacetin or dibutyl sebacate.

In some embodiments of the method, the reverse-enteric coating comprises a hydration aid.

In some embodiments of the method, the hydration aid comprises at least one of a polyvinylpyrrolidone, a vinylpyrrolidone-vinyl acetate copolymer, a polyethylene glycol, mannitol, or hydroxypropyl methylcellulose.

In some embodiments of the method, the enrobed gastric residence dosage form allows the gastric residence system in the folded configuration to assume the open configuration in at least 20 minutes when exposed to an aqueous pH 7.0 environment.

In some embodiments of the method, the enrobed gastric residence dosage form allows the gastric residence system in the folded configuration to assume the open configuration in at least 30 minutes when exposed to an aqueous pH 7.0 environment.

In some embodiments of the method, the enrobed gastric residence dosage form allows the gastric residence system in the folded configuration to assume the open configuration in less than 20 minutes when exposed to an aqueous pH 3.0 environment.

In some embodiments of the method, the enrobed gastric residence dosage form allows the gastric residence system in the folded configuration to assume the open configuration in less than 15 minutes when exposed to an aqueous pH 3.0 environment.

In some embodiments, an enrobed gastric residence dosage form made using the method of any of the embodiments provided herein is provided, wherein the enrobed gastric residence dosage form is used to treat a patient.

In some embodiments of the enrobed gastric residence dosage form, wherein the patient is a human.

In some embodiments, a coated enrobed gastric residence dosage form is provided, the coated enrobed gastric residence dosage form comprising: an enrobed gastric residence system; and a coating comprising a reverse-enteric polymer coating the enrobed gastric residence system, wherein $$\frac{\text{static coefficient of friction of coated enrobed gastric residence dosage form}}{\text{static coefficient of friction of uncoated enrobed gastric residence dosage form}} \le 0.8.$$

In some embodiments of the coated enrobed gastric residence dosage form, a static coefficient of friction of the coated enrobed gastric residence dosage form is less than 0.3.

In some embodiments of the coated enrobed gastric residence dosage form, the static coefficient of friction of the coated enrobed gastric residence dosage form is less than 0.2.

In some embodiments of the coated enrobed gastric residence dosage form, the static coefficient of friction of the coated enrobed gastric residence dosage form is less than 0.1.

In some embodiments of the coated enrobed gastric residence dosage form, $$\frac{\text{static coefficient of friction of coated} \atop \text{enrobed gastric residence dosage form}}{\text{static coefficient of friction of uncoated} \atop \text{enrobed gastric residence dosage form}} \leq 0.5.$$

In some embodiments of the coated enrobed gastric residence dosage form, the static coefficient of friction of the coated enrobed gastric residence dosage form is at least 0.08 less than that of an uncoated enrobed gastric residence dosage form.

In some embodiments of the coated enrobed gastric residence dosage form, the static coefficient of friction of the coated enrobed gastric residence dosage form is at least 0.15 less than that of an uncoated enrobed gastric residence dosage form.

In some embodiments of the coated enrobed gastric residence dosage form, the static coefficient of friction of the coated enrobed gastric residence dosage form is at least 0.2 less than that of an uncoated enrobed gastric residence dosage form.

In some embodiments of the coated enrobed gastric residence dosage form, the reverse-enteric polymer comprises a polymethacrylate.

In some embodiments of the coated enrobed gastric residence dosage form, the coating comprises 10 to 50 wt. % reverse-enteric polymer.

In some embodiments of the coated enrobed gastric residence dosage form, the coating comprises an anti-tacking agent.

In some embodiments of the coated enrobed gastric residence dosage form, the anti-tacking agent comprises at least one of talc or magnesium stearate.

In some embodiments of the coated enrobed gastric residence dosage form, the coating comprises 5 to 30 wt. % anti-tacking agent.

BRIEF DESCRIPTION OF THE DRAWINGS

The invention will now be described, by way of example only, with reference to the accompanying drawings, in which:

FIG. 6A shows an enrobed gastric residence dosage form, according to some embodiments;

FIG. 6B shows an enrobed gastric residence dosage form, according to some embodiments;

FIG. 6C shows a side view of an enrobed gastric residence dosage form, according to some embodiments;

DETAILED DESCRIPTION OF THE INVENTION

Figure 1A:
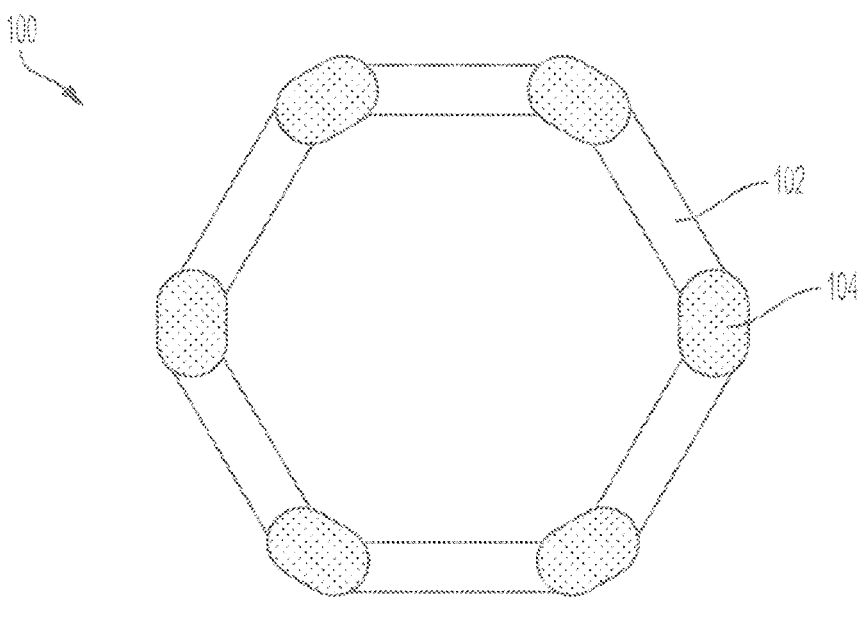
FIG. 1A shows a gastric residence system in an open configuration, according to some embodiments.

Described herein are coatings for gastric residence dosage forms. Provided also are methods of preparing gastric residence dosage forms with disclosed coatings. As described above, gastric residence systems are designed to be swallowed by a patient when the gastric residence system is in a folded or collapsed state (i.e., to enable swallowing and easy passage of the gastric residence system to the patient's stomach). When the gastric residence system enters the patient's stomach, the device unfolds (i.e., opens, deploys). The physical unfolding of the gastric residence system results in a shaped device that is too large to pass through the patient's pyloric valve (i.e., opening between the stomach and the large intestine). The deployed, or expanded, gastric residence system can stay in the patient's stomach for a predetermined period of time (e.g., 24 hours, 48 hours, 7 days, 10 days, etc.).

However, one challenge in particular with gastric residence systems is controlling their opening/unfolding. A gastric residence system that unfolds too early (e.g., in a patient's esophagus) or too late (e.g., in a patient's intestine) is undesirable. A gastric residence system that fails to unfold at all may pass completely through a patient's gastrointestinal tract still in a folded configuration. In each of these hypothetical situations, the gastric residence system fails to properly deliver its therapeutic agent (e.g., active pharmaceutical ingredient) to the patient's stomach.

Further, gastric residence systems are typically administered to a patient in a capsule, as discussed above. However, the two pieces of a conventional capsule can be easily separated to expose the encapsulated therapeutic agent or, in this case, the gastric residence system with the therapeutic agent. Thus, capsules permit easy tampering with the gastric residence system.

Accordingly, coatings for enrobing gastric residence dosage forms provided herein are designed to better control the deployment of gastric residence systems such that enrobed gastric residence dosage forms effectively deliver the therapeutic agent to the patient's stomach. In particular, enrobed gastric residence dosage forms according to embodiments provided herein are more likely to release and allow a gastric residence system to unfold and to assume an open configuration at the desired location and at the desired time within a patient's body. Thus, the particular coating used to prepare the enrobed gastric residence dosage form can be specially formulated to ensure that the gastric residence system does not deploy too early (e.g., in a patient's esophagus), too late (e.g., in a patient's intestine), or not at all.

As used herein, "gastric residence system" is a device comprising a therapeutic agent and is configured to be delivered to a patient's stomach in a folded/collapsed configuration and unfold or open once it reaches a patient's stomach. A "gastric residence dosage form" or "enrobed gastric residence dosage form" comprises a folded gastric residence system and is configured to hold the gastric residence system in a folded configuration until deployment (i.e., in a patient's stomach). A gastric residence dosage form or an enrobed gastric residence dosage form may comprise a coating according to embodiments described herein. Further, "deployment time" is defined as the amount of time it takes a gastric residence system to assume an open configuration.

In some embodiments, an enrobed gastric residence dosage form may include a sleeve or band configured to hold the gastric residence system in a folded configuration. A gastric residence system folded and retained in a folded configuration with a sleeve or band may be enrobed in coating to form an enrobed gastric residence dosage form.

Described below are general principles of gastric residence systems, as well as coating compositions that can be used to enrobe folded gastric residence systems to form enrobed gastric residence dosage forms.

General Principles of Gastric Residence Systems

Provided below is a description of gastric residence systems and how they operate to deliver a therapeutic agent to a patient. In particular, the discussion includes a general description of how gastric residence systems are designed to deliver a therapeutic agent to a patient over an extended period of time, how gastric residence systems are configured for administration, how gastric residence systems are configured to deploy and deliver a therapeutic agent to the stomach of a patient, how the therapeutic agent of a gastric residence system elutes from the device such that the therapeutic agent is delivered to the patient, how the gastric residence system passes through the stomach, and how gastric residence systems are designed to account for some specific safety measures.

Gastric residence systems can be designed to be administered to the stomach of a patient by swallowing, by feeding tube, by gastric tube, etc. Once a gastric residence system is in place in the stomach, it can remain in the stomach for a desired residence time (e.g., three days, seven days, two weeks, etc.). A gastric residence system that is properly in place in a stomach will resist passage through the pyloric valve, which separates the stomach from the small intestine. Gastric residence systems can release a therapeutic agent (i.e., API or drug) over the period of residence with minimal burst release. While residing in the stomach, the system may not interfere with the normal passage of food or other gastric contents. Once the desired residence time has expired, the system passes out of the stomach (i.e., through the pyloric valve) and is readily eliminated from the patient.

To administer a gastric residence system to a patient, the gastric residence system can be folded into a form small enough to be swallowed or otherwise administered. In some embodiments, the folded gastric residence system is retained in a capsule or other container which can be swallowed by the patient. In some cases, the gastric residence system may be delivered to a patient via gastrostomy tube, feeding tube, gastric tube, or other route of administration to the stomach. Examples of folding and encapsulating the gastric residence system are provided in further detail below.

Figure 1B:
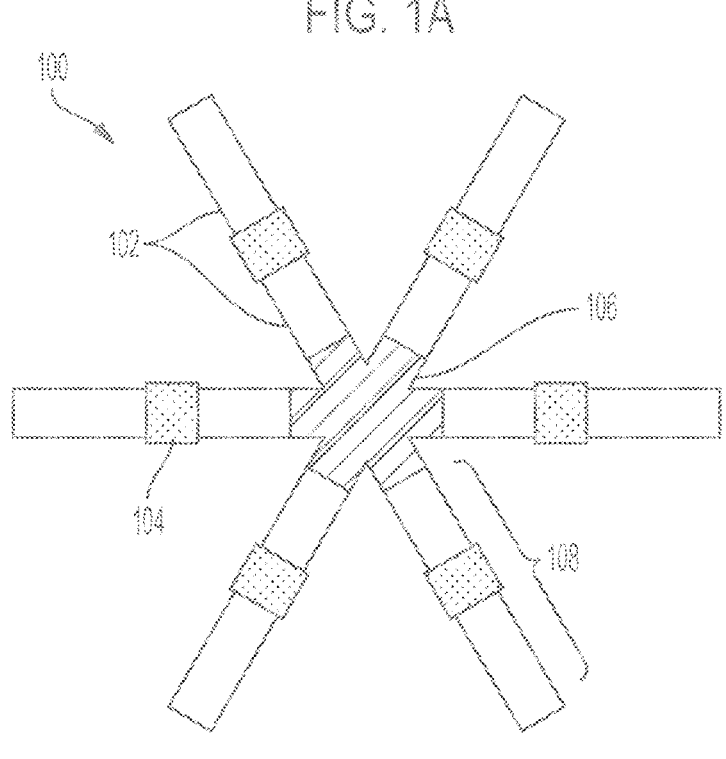
FIG. 1B shows a gastric residence system in an open configuration, according to some embodiments.
Figure 1C:
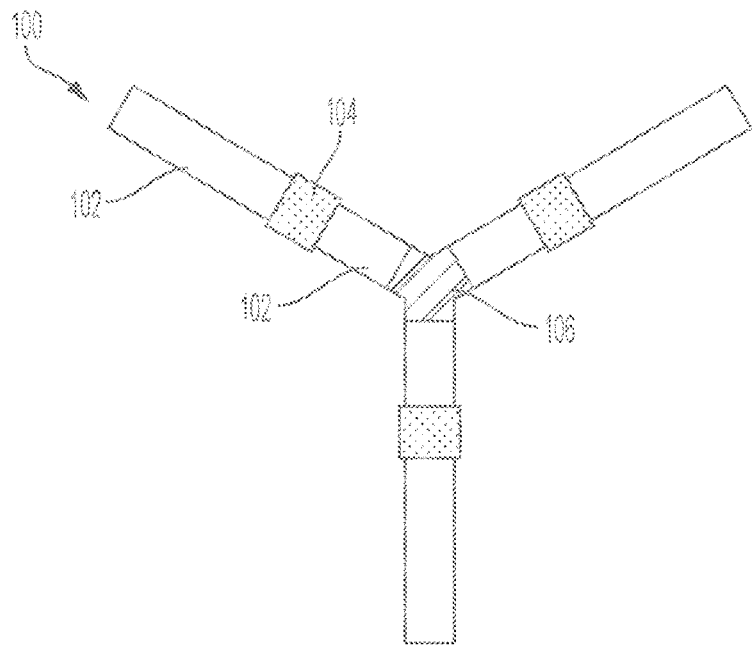
FIG. 1C shows a gastric residence system in an open configuration, according to some embodiments.

FIGS. 1A-1C provide embodiments of foldable or compactable gastric residence systems. Specifically, each foldable or compactable gastric residence system shown in FIGS. 1A-1C is provided in an unfolded configuration.

For example, the ring-shaped design gastric residence system 100 shown in FIG. 1A can be twisted into a double helix. In particular, gastric residence system 100 includes carrier polymer-agent components 102 and couplings 104. In some embodiments, coupling 104 may comprise coupling polymer. In some embodiments, gastric residence system 100 can be folded at one or more coupling polymer joints 104, or twisted into a helix for packaging into a capsule in its folded configuration. Once the capsule dissolves in the stomach, gastric residence system 100 unfolds to the circular shape of its open, or unfolded, configuration, preventing passage through the pyloric valve.

As shown in FIG. 1B, gastric residence system 100 may also be star-shaped (stellate) according to some embodiments. In some embodiments, a star-shaped gastric residence system 100 is constructed around central elastomer 106. Central elastomer 106 may include one or more elongate member 108, or "arms," projecting radially. The arms may be formed by carrier polymer-agent components 102 and couplings 104 comprising coupling polymer. One or more polymer-agent component 102 and coupling 104 together comprise an "arm" of this "star-shaped" configuration. Elastomer 106 enables gastric residence system 100 to be folded for packaging into a capsule.

FIG. 1C shows gastric residence system 100 comprising three "arms" according to some embodiments. This configuration can also include central elastomer 106 from which the three "arms" radially extend. Each of the three arms comprises polymer-agent component 102 and coupling 104 as well.

Figure 2:
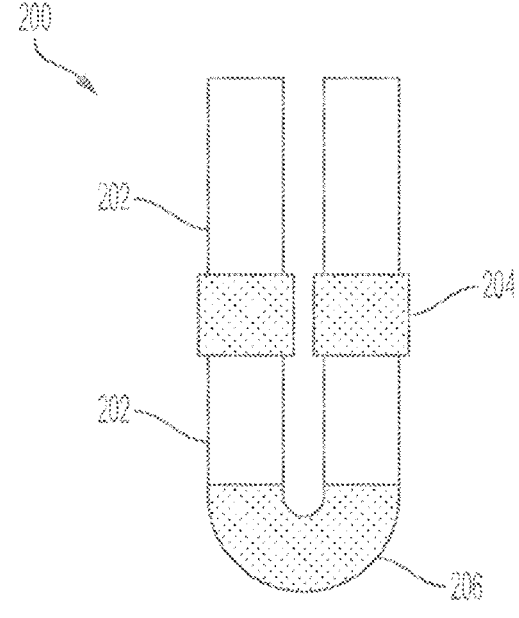
FIG. 2 shows a gastric residence system in a folded configuration, according to some embodiments.

FIG. 2 shows folded gastric residence system 200 according to some embodiments. As shown, the device can fold at central elastomer 206, bringing the ends of each "arm" together. The Figure also shows how the carrier polymer-agent components 102 and couplings 104 of each arm may be oriented in a folded configuration.

The folded configuration of gastric residence system 100 can be bound (i.e., held in a folded configuration) with a sleeve or band. In some embodiments, a gastric residence system in a folded configuration (with or without a sleeve or band) may be encapsulated with a capsule to form a gastric residence dosage form. In some embodiments, the gastric residence dosage form may be coated with a reverse-enteric coating to ensure deployment of the gastric residence system in a patient's stomach.

Once the gastric residence dosage form arrives in the stomach of the patient, any coating and/or capsule of the gastric residence dosage form may dissolve/open and release the folded gastric residence system. Upon release, the gastric residence system unfolds to assume an open configuration, such as a ring shape or a star shape as provided in FIGS. 1A-1C. The dimensions of the open gastric residence system are suitable to prevent passage of the device through the pyloric valve for the period of time during which the device is to reside in the stomach. In some embodiments, the folded gastric residence system can also be secured by a dissolvable retaining band or sleeve that can prevent premature deployment of the gastric residence system.

While in the stomach, the gastric residence system is compatible with digestion and other normal functioning of the stomach or gastrointestinal tract. The gastric residence system does not interfere with or impede the passage of chyme (partially digested food) or other gastric contents which exit the stomach through the pyloric valve into the duodenum.

Once released into the stomach, the therapeutic agent of the gastric residence system begins to take effect. In some embodiments, the gastric residence system comprises a plurality of carrier polymer-agent components. The carrier polymer-agent components may comprise a carrier polymer, a dispersant, and a therapeutic agent (or a salt thereof). The plurality of carrier polymer-agent components are linked together by one or more coupling polymer components. The therapeutic agent may be eluted from the carrier polymer-agent components into the gastric fluid of the patient over the desired residence time of the system. Release of the therapeutic agent is controlled by appropriate formulation of the carrier polymer-agent components.

Additionally, coatings can be applied to outer surfaces of the gastric residence system. The coatings can include additional therapeutic agents or agents that can affect the release of therapeutic agents or the residence duration of the gastric residence system.

Once the desired residence time has expired, the gastric residence system passes out of the stomach. To do so, various components of the gastric residence system are designed to degrade. The specific dimensions of the system are also taken into consideration. In its intact, open configuration, the gastric residence system is designed to resist passage through the pyloric valve. However, coupling polymer components of the gastric residence system are chosen such that they gradually degrade over the specified residence period in the stomach. When the coupling polymer components are sufficiently weakened by degradation, the gastric residence system can break apart into smaller pieces. These smaller pieces are designed to pass through the pyloric valve. The system then passes through the intestines and is eliminated from the patient.

There are some safety considerations to account for during the design and administration of the gastric residence system and the gastric residence dosage form. In particular, it is important that the gastric residence system remain in its folded configuration until it reaches the stomach. If the gastric residence system opens or unfolds prior to reaching the patient's stomach, the patient risks an esophageal obstruction. Similarly, if an intact gastric residence dosage form passes through the pyloric valve without opening and the gastric residence system expanding into its open configuration, there is a risk that it could do so in the patients intestine, resulting in an intestinal obstruction. Accordingly, coatings according to embodiments described herein have been designed to control the deployment of gastric residence systems for improved patient safety.

Examples of gastric residence systems may be found in PCT/US2018/051816, WO 2015/191920, WO 2017/070612, WO 2017/100367, WO 2018/064630, WO 2017/205844, WO 2018/227147, each of which is incorporated herein in its entirety.

Coating Compositions for Enrobing Folded Gastric Residence Systems

Following is a description of coating compositions for enrobing folded gastric residence systems. In some embodiments, a coating composition may include a polymer, a plasticizer, a gelling agent and/or a solvent.

As used herein, the term "coating" may refer to "enrobing." "Enrobing" includes surrounding a folded gastric residence system with a softgel type shell material to form an "enrobed gastric residence system." "Coating" may also refer to a coating applied to the exterior of an enrobed gastric residence device.

Coating compositions for enrobing gastric residence systems have been developed according to embodiments provided herein to enhance gastric residence system deployment performance. Specifically, coating compositions for enrobing gastric residence systems have been developed to retain a gastric residence system in a compacted configuration between the time of administration and the time it reaches the stomach. Once the gastric residence dosage form reaches the stomach, the coating is designed to dissolve rapidly. A rapidly-dissolving coating can ensure that the gastric residence system is released within the stomach before passing through the pyloric valve.

Enrobed gastric residence dosage forms can offer various advantages over gastric residence systems encapsulated in conventional capsules. As mentioned above, a coating for enrobing a folded gastric residence system according to embodiments provided here can protect the therapeutic agent (and in this case, the gastric residence system) from tampering. Additionally, enrobed gastric residence dosage forms can be easier to swallow than gastric residence systems encapsulated only in conventional capsules, which can help reduce the transit time in the esophagus and minimize any chance of the gastric residence system releasing and unfolding in the esophagus.

Additionally, enrobing gastric residence systems with a coating composition according to embodiments provided herein allows for a slippery, non-adhesive surface for ease of swallowing (to prevent esophageal holdups) and a non-tacky and defect-free processing, storage, and shipment phases.

As described above, coating compositions according to embodiments provided herein are designed to protect a patient against esophageal deployment. For example, the deployment time of an enrobed gastric residence dosage form in an aqueous pH 7.0 environment (i.e., the approximate pH of the esophagus) may be from 15 to 120 minutes, from 20 to 60 minutes, or from 20 to 30 minutes. In some embodiments, the deployment time of an enrobed gastric residence dosage form in an aqueous pH 7.0 environment may be less than 120 minutes, less than 100 minutes, less than 80 minutes, less than 60 minutes, less than 50 minutes, less than 40 minutes, less than 30 minutes, less than 25 minutes, or less than 20 minutes. In some embodiments, the deployment time of an enrobed gastric residence dosage form in an aqueous pH 7.0 environment may be more than 15 minutes, more than 20 minutes, more than 25 minutes, more than 30 minutes, more than 40 minutes, more than 50 minutes, more than 60 minutes, more than 80 minutes, or more than 100 minutes.

Coating compositions according to embodiments provided herein can also be designed to rapidly dissolve in a gastric environment. As described above, once a gastric residence dosage form has reached the stomach, it should dissolve rapidly to allow the gastric residence system to deploy in the stomach. If the coating material fails to dissolve rapidly, then the gastric residence dosage form risks passing through the pyloric valve prior to releasing the gastric residence system. Accordingly, coating compositions according to embodiments provided herein are designed to dissolve rapidly and consistently. In some embodiments, the dissolution of the coating material has little or no reliance on a low pH.

For example, an enrobed gastric residence dosage form may deploy after residing in an aqueous pH 3.0 environment from 1 to 60 minutes, from 5 to 45 minutes, or from 10 to 30 minutes. In some embodiments, an enrobed gastric residence dosage form may deploy after residing in an aqueous pH 3.0 environment for more than 1 minutes, more than 2 minutes, more than 3 minutes, more than 4 minutes, more than 5 minutes, more than 10 minutes, more than 15 minutes, more than 20 minutes, more than 25 minutes, more than 30 minutes, more than 35 minutes, more than 40 minutes, more than 45 minutes, more than 50 minutes, or more than 55 minutes. In some embodiments, an enrobed gastric residence dosage form may deploy in an aqueous pH 3.0 environment for less than 60 minutes, less than 55 minutes, less than 50 minutes, less than 45 minutes, less than 40 minutes, less than 35 minutes, less than 30 minutes, less than 25 minutes, less than 20 minutes, less than 15 minutes, less than 10 minutes, less than 5 minutes, less than 4 minutes, less than 3 minutes, or less than 2 minutes.

The thickness of the coating for enrobing gastric residence devices in folded configurations may vary depending on desired properties of the enrobed gastric residence dosage form (e.g., deployment time). In some embodiments, the thickness of the coating enrobing the folded gastric residence system may be from 50 to 700 microns or from 150 to 350 microns thick. In some embodiments, the thickness of the coating enrobing the folded gastric residence system may be more than 50 microns, more than 100 microns, more than 150 microns, more than 200 microns, more than 250 microns, more than 300 microns, more than 350 microns, more than 400 microns, more than 450 microns, more than 500 microns, more than 550 microns, more than 600 microns, or more than 650 microns thick. In some embodiments, the thickness of the coating enrobing the folded gastric residence system may be less than 700 microns, less than 650 microns, less than 600 microns, less than 550 microns, less than 500 microns, less than 450 microns, less than 400 microns, less than 350 microns, less than 300 microns, less than 250 microns, less than 200 microns, less than 150 microns, or less than 100 microns thick. In some embodiments, the coating for enrobing folded gastric residence systems may provide a hermetic seal. For example, the coating may hermetically seal the folded gastric residence system to form an enrobed gastric residence dosage form. In some embodiments, the coating for enrobing folded gastric residence systems may comprise softgel type shell material.

Coating compositions according to embodiments provided herein may include a polymer, a plasticizer, a gelling agent, and/or water.

In some embodiments, the polymer may be pH-responsive polymer such as a water-based polymer dispersion or a reverse-enteric polymer. A suitable water-based polymer dispersion includes Kollicoat® Smartseal. A reverse-enteric polymer can encourage dissolution of the coating in the gastric environment and may provide a moisture barrier to the gastric residence system. The reverse-enteric polymer may also have desirable physiochemical dissolution properties, good film-forming capacity, and may be suitable for pharmaceutical coating methods (e.g., pan-coating). In some embodiments, polymethacrylates are suitable reverse-enteric polymers. For example, Eudragit® polymers may be suitable in some embodiments. Eudragit® polymers include a diverse range of polymethacrylate-based copolymers specifically formulated to aid in targeted drug release. In some embodiments, Eudragit® E, a specific type of poly methacrylate, may be a suitable reverse-enteric polymer. In particular. Eudragit® E dissolves in gastric fluid by the salt formation of its tertiary amine group in pH environments below 5.0. Thus, Eudragit® E can provide a suitable moisture barrier at neutral pH environments (i.e., in the mouth and esophagus). Other materials may also be suitable as a reverse-enteric polymer, such as those that ionize and/or solubilize in acidic environments to provide an enhanced rate of moisture permeation (i.e., access to the underlying capsule or coating layers). However, pH dependence is not a requirement of the polymer itself, but may be achieved with the addition of other excipients in the coating formulation. For example, the coating formulation may include small molecule additives with enhanced solubility at reduced pH (e.g., tertiary amine, imidazole-containing chemical entities, etc.). In some embodiments, the coating composition may include from 10 to 70 wt. %, from 20 to 60 wt. %, or from 30 to 50 wt. % polymer. In some embodiments, the coating composition may include less than 70 wt. %, less than 65 wt. %, less than 60 wt. %, less than 55 wt. %, less than 50 wt. %, less than 45 wt. %, less than 40 wt. %, less than 35 wt. %, less than 30 wt. %, less than 25 wt. %, less than 20 wt. %, or less than 15 wt % polymer. In some embodiments, the coating composition may include more than 10 wt. %, more than 15 wt. %, more than 20 wt. %, more than 25 wt. %, more than 30 wt. %, more than 35 wt. %, more than 40 wt. %, more than 45 wt. %, more than 50 wt. %, more than 55 wt. %, more than 60 wt. %, more than 65 wt. % more than 70 wt. %, more than 75 wt. %, more than 80 wt. %, or more than 85 wt. % polymer.

Plasticizers in the coating composition may reduce brittle-ness by enhancing the flexibility and resilience of the enrobed gastric residence dosage form. Suitable plasticizers may include phthalates, phosphates, citrates, tartrates, adi-pates, sebacates, sulfonamides, succinates, glycolates, glyc-erolates, benzoates, myristates, polyols, halogenated phe-nyls, and poloxamers. Specific compounds that may be used as a plasticizer in the coating formulation may include triacetin, triethyl citrate, polyethylene glycol, and dibutyl sebacate, glycerin, or sorbitol. In some embodiments, the coating composition may include from 10 to 70 wt. %, from 20 to 60 wt. %, or from 30 to 50 wt % plasticizer. In some embodiments, the coating composition may include less than 70 wt. %, less than 65 wt. %, less than 60 wt. %, less than 55 wt. %, less than 50 wt. %, less than 45 wt. %, less than 40 wt. %, less than 35 wt. %, less than 30 wt. %, less than 25 wt. %, less than 20 wt. %, or less than 15 wt. % plasticizer. In some embodiments, the coating composition may include more than 10 wt. %, more than 15 wt. %, more than 20 wt. %, more than 25 wt. %, more than 30 wt. %, more than 35 wt. %, more than 40 wt. %, more than 45 wt. %, more than 50 wt. %, more than 55 wt. %, more than 60 wt. %, more than 65 wt. % more than 70 wt. %, more than 75 wt. %, more than 80 wt. %, or more than 85 wt. % plasticizer.

Coating compositions according to embodiments pro-vided herein include a gelling agent. For example, suitable gelling agents may include gelatin, pullulan, hydroxypropyl methylcellulose, and/or potato starch. If gelatin is used as the gelling agent, the bloom strength of the gelatin may be from 100 to 300 or from 150 to 250. In some embodiments, the bloom strength of the gelatin may be more than 100, more than 150, more than 200, or more than 250. In some embodiments, the bloom strength of the gelatin may be less than 300, less than 250, less than 200, or less than 150.

In some embodiments, the coating composition may include from 30 to 80 wt. %, from 40 to 70 wt. %, or from 50 to 60 wt. % gelling agent. In some embodiments, the coating composition may include less than 80 wt. %, less than 75 wt. %, less than 70 wt. %, less than 65 wt. %, less than 60 wt. %, less than 55 wt. %, less than 50 wt. %, less than 45 wt. %, less than 40 wt. %, or less than 35 wt. % gelling agent. In some embodiments, the coating composi-tion may include more than 30 wt. %, more than 35 wt. %, more than 40 wt. %, more than 45 wt. %, more than 50 wt. %, more than 55 wt. %, more than 60 wt. %, more than 65 wt. %, more than 70 wt. %, or more than 75 wt. % gelling agent.

Coating compositions according to embodiments pro-vided herein may additionally include water. The coating composition may include from 1 to 30 wt. %, from 5 to 25 wt. % or from 10 to 20 wt. % water. In some embodiments, the coating composition may include less than 30 wt. %, less than 25 wt. %, less than 20 wt. %, less than 15 wt. %, less than 10 wt. %, or less than 5 wt. % water. In some embodiments, the coating composition may include more than 1 wt. %, more than 5 wt. %, more than 10 wt. %, more than 15 wt. %, more than 20 wt. %, or more than 25 wt. % water.

Coating compositions according to embodiments pro-vided herein may include additional components other than those already described above. For example, opacifiers, colorants, flavors, and/or preservatives may also be used in coating compositions described herein. A suitable opacifier may include titanium dioxide. Suitable colorants may include FDA-approved dyes and lakes. Suitable flavors include ethyl vanillin and sucrose. Suitable preservatives include parabens, such as methyl paraben or propyl paraben.

Capsules and Sleeves for Folded Gastric Residence Systems

Following is a description of capsules and sleeves for gastric residence systems. In particular, sleeves/bands as described below may be used to hold a gastric residence system in a folded configuration. Capsules may be used to encapsulate the gastric residence system (with or without a sleeve) and control when the gastric residence system is released in a patient's stomach. Once encapsulated (with a sleeve and/or band), the gastric residence system may be enrobed with a coating material to form an enrobed gastric residence dosage form.

In addition to the coating, a sleeve or band and/or a capsule may also be used to contain the compacted gastric residence system for administration. For example, sleeves/bands as described below may be used to hold a gastric residence system in a folded configuration, and a coating may be used to enrobe the gastric residence system (with or without a sleeve).

Sleeves for Mechanically Holding the Gastric Residence System in a Folded Configuration In some embodiments, gastric residence dosage forms described herein may include a "sleeve" or "band". A sleeve or band may bind a gastric residence system into a folded configuration. When used together with a coating as described above, a sleeve may reduce outward pressure on the shell. This can reduce any risk of coating failure and premature deployment of the gastric residence system. Moreover, a sleeve provides a second layer for the gastro-intestinal tract to break down (when used together with a coating). Thus, in the event of coating failure, the sleeve provides a second layer of protection against premature deployment of the gastric residence system.

Figure 3A:
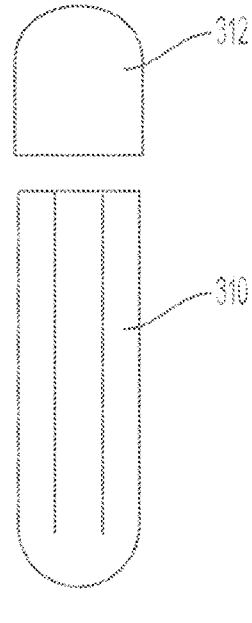
FIG. 3A shows a folded gastric residence system and a sleeve, according to some embodiments.
Figure 3B:
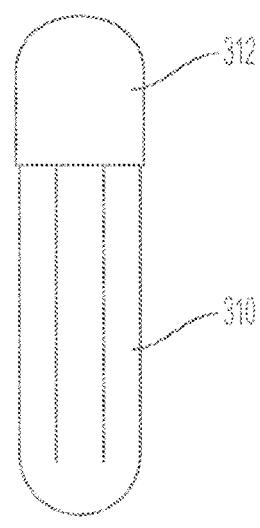
FIG. 3B shows a sleeved gastric residence system, according to some embodiments.

FIG. 3B shows compacted/folded gastric residence sys-tem 310 bound by sleeve 312 according to some embodi-ments. As shown, gastric residence system 302, in its folded configuration, is capped off at one end by sleeve 312.

Figures 4A, 4B, 4C, 4D:
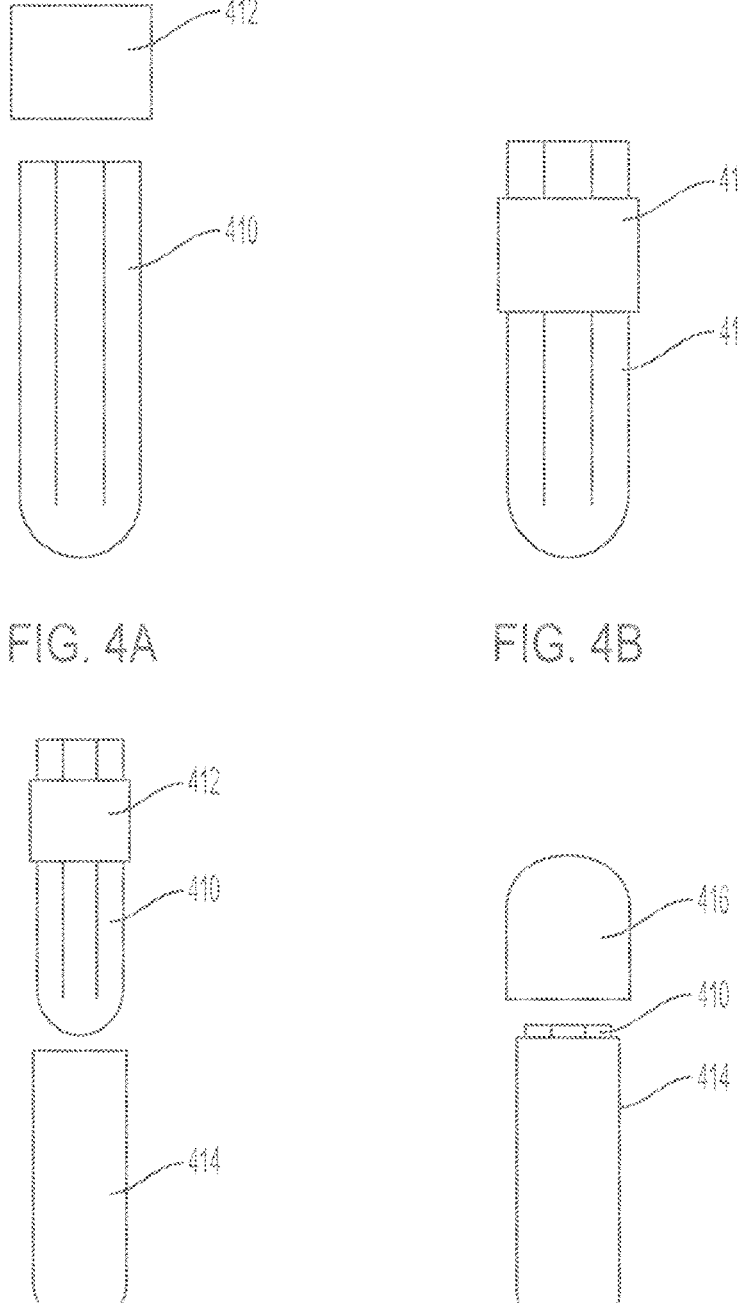
FIG. 4A a folded gastric residence system and a sleeve, according to some embodiments.
FIG. 4B shows a sleeved gastric residence system, according to some embodiments.
FIG. 4C shows a sleeved gastric residence system and a body portion of a two-piece capsule, according to some embodiments.
FIG. 4D shows a sleeved gastric residence system placed inside a body portion of a two-piece capsule, and a cap portion of a two-piece capsule, according to some embodiments.

FIG. 4B shows a compacted/folded gastric residence system 410 bound by sleeve 412 according to some embodi-ments. Unlike sleeve 312 of FIG. 3B, sleeve 412 of FIG. 4B includes two open ends. Thus, compacted/folded gastric residence system 410 passes through sleeve 412 such that gastric residence system 410 is exposed at both open ends of sleeve 412.

In some embodiments, a sleeve may be gelatin-based. In some embodiments, a sleeve may be hydroxypropyl meth-ylcellulose (HPMC)-based or pullulan-based. Other suitable materials (e.g., carrageenan, starch, cellulose, etc.) may also be included in the sleeves. For example, suitable sleeves can include VCaps® HPMC, VCaps® Plus HPMC, Plantcapst, or ConiSnap®.

In some embodiments, the sleeve size and/or thickness may be optimized to control deployment time of a gastric residence system. For example, a sleeve having a thinner shell thickness may be used to release the gastric residence system faster. In some embodiments, a sleeve having a thicker shell thickness may be used to release the gastric residence system slower. In some embodiments, a sleeve having a smaller length and/or width may be used to control the release of a gastric residence system from the gastric residence dosage form. In some embodiments, a sleeve having a larger length and/or width may be used to control the release of a gastric residence system from the gastric residence dosage form. For example, a sleeve having a larger length/width may help delay the release of a gastric residence system. In some embodiments, a sleeve having a shorter length/width may be used to speed the release of a gastric residence system.

Additionally, some embodiments may include a wicking material between the sleeve and a folded gastric residence system. A wicking material may help a gastric residence system deploy faster. In some embodiments, the wicking material may comprise a hydrophilic polymer, a hygroscopic polymer, a hygroscopic wetting agent, and/or a humectant. Polymeric examples may include polysaccharide-based polymers such as hydroxypropyl methylcellulose, carboxymethylcellulose, starch, pectin, chitosan, alginate, other natural or semi-synthetic polymers like gelatin collagen, silk fibroin, and/or non-cellulosic synthetic polymers like poly-ethylene glycol, polyethyl glycol-polypropylene glycol di- and tri-block copolymers, poly vinylpyrrolidone, and derivatives thereof. Non-polymeric wicking materials may include wetting agents and humectants including polysorbates, glycerol, propanediol, sugars such as sucrose, glucose, dextrose, mannitol, maltitol, mannose and various salts.

Capsules for Folded Gastric Residence Dosage Forms

In addition to a "sleeve" or "band", as described above and provided in FIGS. 3A-C and 4A-C (described in detail below), a capsule may also be used to retain the gastric residence system in a folded configuration until the dosage form reaches the stomach. A capsule may be used in addition to, or in lieu of, a sleeve. Once a gastric residence system is encapsulated, it may be enrobed in a coating to form an enrobed gastric residence dosage form. Provided below is a discussion of capsules according to some embodiments.

Capsules according to embodiments provided herein may be designed to rapidly dissolve and/or open in a gastric environment. As described above, once an enrobed gastric residence dosage form has reached the stomach, it should dissolve and/or open rapidly to allow the gastric residence system to release and unfold in the stomach. If the capsule fails to dissolve/open rapidly, then the enrobed gastric residence dosage form risks passing through the pyloric valve prior to releasing the gastric residence system. Accordingly, capsules according to embodiments provided herein are designed to dissolve/open rapidly and consistently. In some embodiments, the dissolution/opening of the capsule and/or sleeve has little or no reliance on a low pH.

In some embodiments, the capsules may be gelatin-based. In some embodiments, the capsules and/or sleeves may be hydroxypropyl methylcellulose (HPMC)-based or pullulan-based. Other suitable materials (e.g., carrageenan, starch, cellulose, etc.) may also be included in the capsules and/or sleeves. For example, suitable capsules can include VCaps® HPMC, VCaps® Plus HPMC, Plantcaps®, or Coni-Snap®.

In some embodiments, the capsule size and/or thickness may be optimized to further control the deployment time of a gastric residence system. For example, a capsule having a thinner shell thickness may be used to release the gastric residence system faster. In some embodiments, a capsule having a thicker shell thickness may be used to release the gastric residence system slower. In some embodiments, a capsule having a smaller length and/or width may be used to control the release of a gastric residence system from the gastric residence dosage form. In some embodiments, a capsule having a larger length and/or width may be used to control the release of a gastric residence system from the gastric residence dosage form. For example, a capsule having a larger length/width may help delay the release of a gastric residence system. In some embodiments, a capsule having a shorter length/width may be used to speed the release of a gastric residence system.

A folded gastric residence system (bound with a sleeve or unbound) may be inserted into a two-piece capsule using any suitable encapsulation technique. For example, a gastric residence system may be manually folded and encapsulated. In some embodiments, the sleeve may be a size 0 or 0EL capsule cap. Once bound by the sleeve, the gastric residence system may be encapsulated with the sleeved end of the gastric residence system in the body of the two-piece capsule. If a 0 or 0EL capsule cap is used to sleeve the gastric residence system, for example, a slightly larger capsule (e.g., a size 00EL capsule) may be used to encapsulate the sleeved gastric residence system. In some embodiments, a folded gastric residence system may be encapsulated without a sleeve.

Figure 3C:
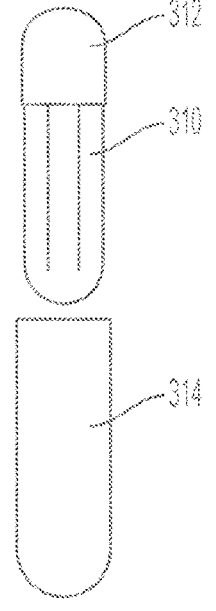
FIG. 3C shows a sleeved gastric residence system and a body portion of a two-piece capsule, according to some embodiments.
Figure 3D:
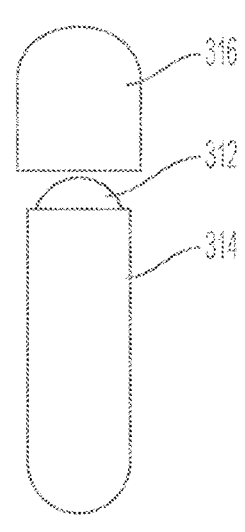
FIG. 3D shows a sleeved gastric residence system placed inside a body portion of a two-piece capsule, and a cap portion of a two-piece capsule, according to some embodiments.

FIGS. 3A-3D and FIG. 4A-4D show the steps of encapsulation according to some embodiments. Sleeve 312 of FIGS. 3A-3D is a full cap that fits on one end of folded gastric residence system 310. Sleeve 412 of FIGS. 4A-4D has a cylindrical shape with an open top and an open bottom. In particular, FIG. 3A shows a folded gastric residence system 310 with sleeve 312. FIG. 3B shows sleeve 312 binding gastric residence system 310 in a folded configuration. FIG. 3C shows gastric residence system 310 including sleeve 312 being inserted into body 314 of a two-piece capsule. FIG. 3D shows body 314 including the sleeve 312 and gastric residence system being capped off with cap 316 of the two-piece capsule. The encapsulated gastric residence system of FIG. 3D may then be enrobed with a coating according to embodiments provided herein to form an enrobed gastric residence dosage form.

Similarly, FIG. 4A shows a folded gastric residence system 410 with sleeve 412. FIG. 4B shows sleeve 412 binding gastric residence system 410 in a folded configuration. FIG. 4C shows gastric residence system 410 including sleeve 412 being inserted into body 414 of a two-piece capsule. FIG. 4D shows the body 414 including the sleeved gastric residence system 410 being capped off with cap 416 of the two-piece capsule. The encapsulated gastric residence system of FIG. 4D may then be enrobed with a coating according to embodiments provided herein to form an enrobed gastric residence dosage form.

Figure 5A:
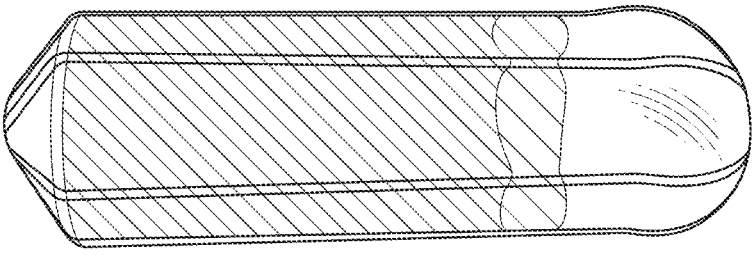
FIG. 5A shows an enrobed gastric residence dosage form, according to some embodiments.
Figure 5B:
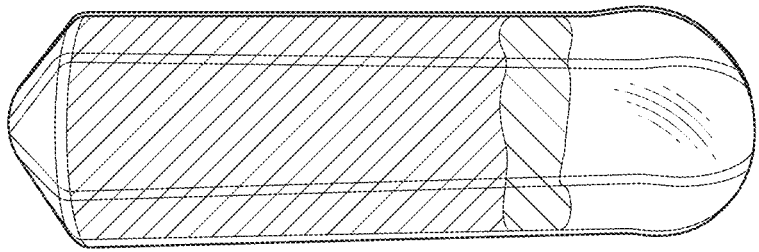
FIG. 5B shows an enrobed gastric residence dosage form, according to some embodiments.
Figure 5C:
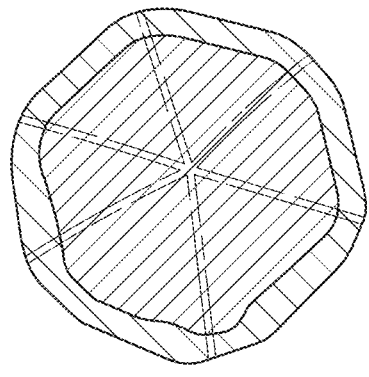
FIG. 5C shows a side view of an enrobed gastric residence dosage form, according to some embodiments.

Additionally, FIGS. 5A-C and FIGS. 6A-C show examples of enrobed gastric residence dosage forms according to some embodiments. In particular, FIG. 5A-5C show views of an enrobed gastric residence dosage form comprising a sleeve to hold the gastric residence system in a folded configuration. Because the enrobed coating of FIGS. 5A-5C is translucent, the folded gastric residence system is also shown underneath the coating.

FIGS. 6A-6C show views of an enrobed gastric residence dosage form comprising a sleeve and a capsule according to some embodiments. In particular, the enrobed gastric residence dosage forms of FIGS. 6A-6C include a sleeve holding the folded gastric residence system in its folded configuration and a capsule encapsulating the folded gastric residence system. As compared to the enrobed gastric residence dosage forms of FIGS. 5A-5C, the thickness of the coating material shown in FIGS. 6A-6C is more consistent. Thus, including encapsulating the folded gastric residence system in a capsule prior to enrobing may provide a more consistent coating layer and more predictable deployment behavior (described in the Example below).

Reverse-Enteric Coatings for Enrobed Gastric Residence Dosage Forms

Following is a description of reverse-enteric coatings for enrobed gastric residence dosage forms. In addition to the coatings for enrobing folded gastric residence systems described above, a reverse-enteric coating may also be applied to an enrobed gastric residence dosage form to help control deployment of the folded gastric residence system. In particular, reverse-enteric coatings described below may be used to delay dissolution/opening of the enrobed gastric residence dosage form when the gastric residence dosage form is in the esophagus. In some embodiments, reverse-enteric coatings described below may speed up opening when the enrobed gastric residence dosage form is in the stomach. As described below, reverse-enteric coatings may provide a protective moisture barrier, encourage gastric dissolution, encourage passage through the esophagus, and provide a more pleasant administration experience for the patient.

As mentioned above, reverse-enteric coating compositions provided herein may delay the time at which the enrobed gastric residence dosage form releases a gastric residence system and allows it to assume an open configuration to help prevent premature deployment in a patient's esophagus (i.e., pH 7.0). For example, an enrobed gastric residence dosage form comprising a reverse-enteric coating may release a folded gastric residence system and allow it to assume an open configuration after residing in an aqueous pH 7.0 environment from 20 to 120 minutes, from 30 to 90 minutes, or from 40 to 60 minutes. In some embodiments, an enrobed gastric residence dosage form comprising a reverse-enteric coating may release a folded gastric residence system and allow it to assume an open configuration after residing in an aqueous pH 7.0 environment for less than 120 minutes, less than 100 minutes, less than 80 minutes, less than 60 minutes, less than 50 minutes, less than 40 minutes, or less than 30 minutes. In some embodiments, an enrobed gastric residence dosage form comprising a reverse-enteric coating may release a gastric residence system and allow it to assume an open configuration after residing in an aqueous pH 7.0 environment for more than 20 minutes, more than 30 minutes, more than 40 minutes, more than 50 minutes, more than 60 minutes, more than 80 minutes, or more than 100 minutes. The time at which it takes an enrobed gastric residence dosage form comprising a reverse-enteric coating to open in an esophagus may be longer than the amount of time it takes the enrobed gastric residence dosage form comprising the reverse-enteric coating to pass from a patient's mouth, through the patient's esophagus, and to the patient's stomach.

Reverse-enteric coatings as provided herein have also been developed to encourage rapid dissolution/opening of the enrobed gastric residence dosage form and thus, release of the folded gastric residence system encapsulated within. As discussed above, rapid opening of the enrobed gastric residence dosage form and release of the folded gastric residence system in the stomach (e.g., pH 3.0) can help prevent an enrobed gastric residence dosage form from passing through the pyloric valve too early. Without a reverse-enteric coating according to embodiments provided herein, the enrobed gastric residence dosage form may take significantly longer to open and release in a patient's stomach. However, in some embodiments, an enrobed gastric residence dosage form comprising a reverse-enteric coating may release a folded gastric residence system and allow it to assume an open configuration after residing in an aqueous pH 3.0 environment from 10 seconds to 30 minutes, from 30 seconds to 20 minutes, or from 1 minute to 10 minutes. In some embodiments, an enrobed gastric residence dosage form comprising a reverse-enteric coating may release a folded gastric residence system and allow it to assume an open configuration after residing in an aqueous pH 3.0 environment for more than 10 seconds, more than 20 seconds, more than 30 seconds, more than 40 seconds, more than 50 seconds, more than 1 minute, more than 2 minutes, more than 3 minutes, more than 4 minutes, more than 5 minutes, more than 10 minutes, more than 15 minutes, more than 20 minutes, or more than 25 minutes. In some embodiments, an enrobed gastric residence dosage form comprising a reverse-enteric coating may release a folded gastric residence system and allow it to assume an open configuration after residing in an aqueous pH 3.0 environment for less than 30 minutes, less than 25 minutes, less than 20 minutes, less than 15 minutes, less than 10 minutes, less than 5 minutes, less than 4 minutes, less than 3 minutes, less than 2 minutes, less than 1 minute, less than 50 seconds, less than 40 seconds, less than 30 seconds, or less than 20 seconds.

The thickness of the reverse-enteric coating may vary depending on desired properties of the enrobed gastric residence dosage form (e.g., deployment time). In some embodiments, the thickness of the reverse-enteric coating may be from 5 to 200 microns or from 5 to 100 microns. In some embodiments, the thickness of the reverse-enteric coating may be more than 5 microns, more than 25 microns, more than 50 microns, more than 75 microns, more than 100 microns, more than 125 microns, more than 150 microns, more than 175 microns, more than 200 microns, more than 225 microns, more than 150 microns, or more than 175 microns. In some embodiments, the thickness of the reverse-enteric coating may be less than 200 microns, less than 175 microns, less than 150 microns, less than 125 microns, less than 100 microns, less than 75 microns, less than 50 microns, or less than 25 microns.

In some embodiments, the static coefficient of friction of an enrobed gastric residence dosage form coated with a reverse-enteric low-friction static coefficient polymer coating may be less than that of an uncoated enrobed gastric residence dosage form. In some embodiments, the static coefficient of friction of a coated enrobed gastric residence dosage form may be from 0.02 to 0.3 or from 0.05 to 0.2. In some embodiments, the static coefficient of friction of a coated enrobed gastric residence dosage form may be less than 0.3, less than 0.25, less than 0.2, less than 0.15, less than 0.1, or less than 0.05. In some embodiments, the static coefficient of friction of a coated enrobed gastric residence dosage form may be more than 0.02, more than 0.05, more than 0.1, more than 0.15, more than 0.2, or more than 0.25. In some embodiments, $$\frac{\text{static coefficient of friction of coated enrobed gastric residence dosage form}}{\text{static coefficient of friction of uncoated enrobed gastric residence dosage form}}$$

may be 0.2-0.8. In some embodiments, $$\frac{\text{static coefficient of friction of coated enrobed gastric residence dosage form}}{\text{static coefficient of friction of uncoated enrobed gastric residence dosage form}}$$

may be less than 0.8, less than 0.7, less than 0.6, less than 0.5, less than 0.4, or less than 0.3. In some embodiments, $$\frac{\text{static coefficient of friction of coated enrobed gastric residence dosage form}}{\text{static coefficient of friction of uncoated enrobed gastric residence dosage form}}$$

may be more than 0.2, more than 0.3, more than 0.4, more than 0.5, more than 0.6, or more than 0.7.

In some embodiments, the static coefficient of friction of a coated enrobed gastric residence dosage form may be from 5-80%, from 20-80%, or from 50-80% that of an uncoated enrobed gastric residence dosage form. In some embodiments, the static coefficient of friction of a coated enrobed gastric residence dosage form may be less than 80%, less than 70%, less than 60%, less than 50%, less than 40%, less than 30%, less than 20%, or less than 10% that of an uncoated dosage form. In some embodiments, the static coefficient of friction of a coated enrobed gastric residence dosage form may be more than 5%, more than 10%, more than 20%, more than 30%, more than 40%, more than 50%, more than 60%, or more than 70% that of an uncoated enrobed gastric residence dosage form. In some embodiments, the static coefficient of friction of a coated enrobed gastric residence dosage form may be from 0.05 to 0.35, or from 0.1 to 0.2 less than that of an uncoated enrobed gastric residence dosage form. In some embodiments, the static coefficient of friction of a coated enrobed gastric residence dosage form may be less than 0.35, less than 0.3, less than 0.25, less than 0.2, less than 0.15, or less than 0.1, or less than 0.08 less than that of an uncoated enrobed gastric residence dosage form. In some embodiments, the static coefficient of friction of a coated enrobed gastric residence dosage form maybe more than 0.05, more than 0.08, more than 0.1, more than 0.15, more than 0.2, more than 0.25, or more than 0.3 less than that of an uncoated enrobed gastric residence dosage form.

Reverse-enteric coatings according to embodiments provided herein may include a polymer, a plasticizer, an anti-tacking agent, and/or a hydration aid.

In some embodiments, the polymer may be a reverse-enteric polymer. A reverse-enteric polymer can encourage dissolution of the enrobed gastric residence dosage form in a gastric environment (e.g., pH 3.0). A suitable reverse-enteric polymer may have desirable physiochemical dissolution properties, have good film-forming capacity, and be suitable for pharmaceutical coating methods (e.g., pan-coating). In some embodiments, poly methacrylates are suitable reverse-enteric polymers. For example, Eudragit® polymers may be suitable in some embodiments. Eudragit® polymers include a diverse range of polymethacrylate-based copolymers specifically formulated to aid in targeted drug release. In some embodiments. Eudragit® E may be a suitable reverse-enteric polymer. In particular, Eudragit® E dissolves in gastric fluid by the salt formation of its tertiary amine group in pH environments below 5.0. Thus, Eudragit® E can provide a suitable moisture barrier at neutral pH environments (i.e., in the mouth and esophagus). Another example of a Eudragit® polymer that may be suitable is Eudragit® E PO, which is readily soluble in the stomach. However, other materials may also be suitable as a reverse-enteric polymer, such as those that ionize and/or solubilize in acidic environments to provide an enhanced rate of moisture permeation (i.e., access to the underlying capsule or coating layers). However. pH dependence is not a requirement of the polymer itself, but may be achieved with the addition of other excipients in the coating formulation. For example, the coating formulation may include small molecule additives with enhanced solubility at reduced pH (e.g., tertiary amine, imidazole-containing chemical entities, etc.). In some embodiments, a dry reverse-enteric coating composition on an enrobed gastric residence dosage form may include from 40 to 95 wt. %, from 50 to 80 wt. %, or from 60 to 70 wt. % polymer to total solids. In some embodiments, a dry reverse-enteric coating composition on an enrobed gastric residence dosage form may include less than 95 wt. %, less than 90 wt. %, less than 85 wt. %, less than 80 wt. %, less than 75 wt. %, less than 70 wt. %, less than 65 wt. %, less than 60 wt. %, less than 55 wt. %, less than 50 wt. %, or less than 45 wt. % polymer to total solids. In some embodiments, a dry reverse-enteric coating composition on an enrobed gastric residence dosage form may include more than 40 wt. %, more than 45 wt. %, more than 50 wt. %, more than 55 wt. %, more than 60 wt. %, more than 65 wt. %, more than 70 wt. %, more than 75 wt. % polymer, more than 80 wt. %, more than 85 wt. %, or more than 90 wt. % polymer to total solids.

In some embodiments, a liquid reverse-enteric coating composition (i.e., in solution, prior to drying on the surface of an enrobed gastric residence dosage form) may include from 3 to 30 wt. % polymer, from 5 to 25 wt. % polymer, or from 5 to 20 wt. % polymer. In some embodiments, a liquid reverse-enteric coating composition may include more than 3 wt. %, more than 5 wt. %, more than 8 wt. %, more than 10 wt. %, more than 12 wt. %, more than 15 wt. %, more than 18 wt. %, more than 20 wt. %, or more than 25 wt. % polymer. In some embodiments, a liquid reverse-enteric coating composition may include less than 30 wt. %, less than 28 wt. %, less than 25 wt. %, less than 23 wt. %, less than 20 wt. %, less than 18 wt. %, less than 15 wt. %, less than 12 wt. %, less than 10 wt. %, less than 8 wt. %, or less than 5 wt. % polymer.

Plasticizers in the coating formulation may reduce brittleness by enhancing the flexibility, resilience, and adhesion of the coating to the underlying gastric residence dosage form surface. Suitable plasticizers may include phthalates, phosphates, citrates, tartrates, adipates, sebacates, sulfonamides, succinates, glycolates, glycerolates, benzoates, myristates, halogenated phenyls, and poloxamers. Specific compounds that may be used as a plasticizer in the coating formulation can include triacetin, triethyl citrate, polyethylene glycol, and dibutyl sebacate. In some embodiments, a dry reverse-enteric coating composition on an enrobed gastric residence dosage form may include from 1 to 30 wt. %, from 1 to 20 wt. %, or from 1 to 10 wt. % plasticizer to total solids. In some embodiments, a dry reverse-enteric coating composition on an enrobed gastric residence dosage form may include less than 30 wt. %, less than 25 wt. %, less than 20 wt. %, less than 15 wt. %, less than 10 wt. %, less than 9 wt. %, less than 8 wt. %, less than 7 wt. %, less than 6 wt. %, less than 5 wt. %, less than 4 wt. %, less than 3 wt. %, or less than 2 wt. % plasticizer to total solids. In some embodiments, a dry reverse-enteric coating composition on an enrobed gastric residence dosage form may include more than 1 wt. %, more than 2 wt. %, more than 3 wt. %, more than 4 wt. %, more than 5 wt. %, more than 6 wt. %, more than 7 wt. %, more than 8 wt. %, more than 9 wt. %, more than 10 wt. %, more than 15 wt. %, more than 20 wt. %, or more than 25 wt. % plasticizer to total solids.

In some embodiments, a liquid reverse-enteric coating composition (i.e., in solution, prior to drying on the surface of an enrobed gastric residence dosage form) may include from 0.1 to 5.0 wt. %, from 0.2 to 3.0 wt. %, or from 0.3 to 1.0 wt. % plasticizer. In some embodiments, a liquid reverse-enteric coating composition may include more than 0.1 wt. %, more than 0.2 wt. %, more than 0.3 wt. %, more than 0.4 wt. %, more than 0.5 wt. %, more than 0.6 wt. %, more than 0.7 wt. %, more than 0.8 wt. %, more than 0.9 wt. %, more than 1.0 wt. %, more than 1.5 wt. %, more than 2.0 wt. %, more than 2.5 wt. %, more than 3.0 wt. %, or more than 4.0 wt. % plasticizer. In some embodiments, a liquid reverse-enteric coating composition may include less than 5.0 wt. %, less than 4.0 wt. %, less than 3.5 wt. %, less than 3.0 wt. %, less than 2.5 wt %, less than 2.0 wt %, 1.5 wt. %, less than 1.0 wt. %, less than 0.9 wt. %, less than 0.8 wt. %, less than 0.7 wt. % less than 0.6 wt %, less than 0.5 wt. %, less than 0.4 wt. %, less than 0.3 wt. %, or less than 0.2 wt. % plasticizer.

An anti-tacking agent in the reverse-enteric coating formulation may help prevent tackiness during process and storage. Additionally, certain anti-tacking agents may improve the lubricity of the enrobed gastric residence dosage forms and provide a glossy and smooth surface finish. Suitable anti-tacking agents may include bulk-acting agents (e.g., talc) and surface-acting agents (e.g., magnesium stearate). In some embodiments, magnesium stearate in particular may help decrease the static coefficient of friction of a coated encapsulated gastric residence system. In some embodiments, a coating comprising magnesium stearate may be able to lower the static coefficient of friction to less than 0.1, or such that $$\frac{\text{static coefficient of friction of coated}}{\text{enrobed gastric residence dosage form}} \frac{}{\text{static coefficient of friction of uncoated}} \frac{}{\text{enrobed gastric residence dosage form}}$$

is less than or equal to 0.4, some embodiments, a dry reverse-enteric coating composition on an enrobed gastric residence dosage form may include from 1 to 40 wt. %, from 1 to 25 wt. %, or from 1 to 10 wt. % anti-tacking agent to total solids. In some embodiments, a dry reverse-enteric coating composition on an enrobed gastric residence dosage form may include less than 40 wt. %, less than 35 wt. %, less than 30 wt. %, less than 25 wt. %, less than 20 wt. %, less than 15 wt. % less than 10 wt. %, less than 9 wt. %, less than 8 wt. %, less than 7 wt %, less than 6 w. %, less than 5 wt. %, less than 4 wt. %, less than 3 wt. %, or less than 2 wt. % anti-tacking agent to total solids. In some embodiments, a dry reverse-enteric coating composition on an enrobed gastric residence dosage form may include more than 1 wt. %, more than 2 wt. %, more than 3 wt. %, more than 4 wt. %, more than 5 wt. %, more than 6 wt. %, more than 7 wt. %, more than 8 wt. %, more than 9 wt. %, more than 10 wt. %, more than 15 wt. %, more than 20 wt. %, more than 25 wt. %, more than 30 wt. %, or more than 35 wt. % anti-tacking agent to total solids.

In some embodiments, a liquid reverse-enteric coating composition (i.e., in solution, prior to drying on the surface of an enrobed gastric residence dosage form) may include from 0.1 to 5.0 wt. %, from 0.2 to 3.0 wt. %, or from 0.3 to 1.0 wt. % anti-tacking agent. In some embodiments, a liquid reverse-enteric coating composition may include more than 0.1 wt. %, more than 0.2 wt. %, more than 0.3 wt. %, more than 0.4 wt. %, more than 0.5 wt. %, more than 0.6 wt. %, more than 0.7 wt. %, more than 0.8 wt. %, more than 0.9 wt.

%, more than 1.0 wt. %, more than 1.5 wt. %, more than 2.0 wt. %, more than 2.5 wt. %, more than 3.0 wt. %, or more than 4.0 wt. % anti-tacking agent. In some embodiments, a liquid reverse-enteric coating composition may include less than 5.0 wt. %, less than 4.0 wt. %, less than 3.5 wt. %, less than 3.0 wt %, less than 2.5 wt. %, less than 2.0 wt. %, 1.5 wt. %, less than 1.0 wt. %, less than 0.9 wt. %, less than 0.8 wt. %, less than 0.7 wt. %, less than 0.6 wt. %, less than 0.5 wt. %, less than 0.4 wt %, less than 0.3 wt. %, or less than 0.2 wt. % anti-tacking agent.

Reverse-enteric coating compositions according to embodiments provided herein may include a hydration aid. A hydration aid may help achieve faster dissolution of the enrobed gastric residence dosage form in the gastric environment by accelerating hydration. Suitable hydration aids may include Kollidon PVP12, Kollidon VA64, PEG 1000, low viscosity hydroxypropyl methylcellulose, and crystalline mannitol. In some embodiments, a dry reverse-enteric coating composition on an enrobed gastric residence dosage form may include from 2 to 50 wt. %, from 5 to 40 wt. %, or from 10 to 30 wt. % hydration aid to total solids.

In some embodiments, a dry reverse-enteric coating composition on an enrobed gastric residence dosage form may include less than 50 wt. %, less than 45 wt. %, less than 40 wt. %, less than 35 wt. %, less than 30 wt. %, less than 25 wt. %, less than 20 wt. %, less than 15 wt. %, less than 10 wt. %, or less than 5 wt. % hydration aid to total solids. In some embodiments, a dry reverse-enteric coating composition on an enrobed gastric residence dosage form may include more than 2 wt. %, more than 5 wt. %, more than 10 wt. %, more than 15 wt %, more than 20 wt. %, more than 25 wt. %, more than 30 wt. %, more than 35 wt. %, more than 40 wt. %, or more than 45 wt. % hydration aid to total solids.

In some embodiments, a liquid reverse-enteric coating composition (i.e., in solution, prior to drying on the surface of an enrobed gastric residence dosage form) may include from 0.1 to 5.0 wt. %, from 0.2 to 3.0 wt. %, or from 0.3 to 1.0 wt. % hydration aid. In some embodiments, a liquid reverse-enteric coating composition may include more than 0.1 wt. %, more than 0.2 wt. %, more than 0.3 wt. %, more than 0.4 wt. %, more than 0.5 wt. %, more than 0.6 wt. %, more than 0.7 wt. %, more than 0.8 wt. %, more than 0.9 wt. %, more than 1.0 wt. %, more than 1.5 wt. %, more than 2.0 wt. %, more than 2.5 wt. %, more than 3.0 wt. %, or more than 4.0 wt. % hydration aid. In some embodiments, a liquid reverse-enteric coating composition may include less than 5.0 wt. %, less than 4.0 wt. %, less than 3.5 wt. %, less than 3.0 wt. %, less than 2.5 wt. %, less than 2.0 wt. %, 1.5 wt. %, less than 1.0 wt %, less than 0.9 wt. %, less than 0.8 wt. %, less than 0.7 wt. %, less than 0.6 wt. %, less than 0.5 wt. %, less than 0.4 wt. %, less than 0.3 wt. %, or less than 0.2 wt. % hydration aid.

Reverse-enteric coating compositions according to embodiments provided herein may be soluble in a variety of solvents. For example, reverse-enteric coating compositions may be soluble in aqueous solvents and/or organic solvents. Examples of suitable solvents include isopropyl alcohol, acetone, and ethyl acetate. In some embodiments, a liquid reverse-enteric coating composition in solution may include from 55 to 97 wt. % solvent. In some embodiments, a liquid reverse-enteric coating composition in solution may include more than 55 wt %, more than 60 wt. %, more than 65 wt. %, more than 70 wt. %, more than 75 wt. %, more than 80 wt. %, more than 85 wt. %, more than 90 wt. %, or more than 95 wt. % solvent. In some embodiments, a liquid reverse-enteric coating composition in solution may include less than 97 wt. %, less than 95 wt. %, less than 90 wt. %, less than 85 wt. %, less than 80 wt. %, less than 75 wt. %, less than 70 wt. %, less than 65 wt. %, or less than 60 wt. % solvent.

Reverse-enteric coating compositions according to embodiments provided herein may include additional components other than those already described above. For example, a pH-modifying buffer may be used to help accelerate dissolution of the reverse-enteric coating in a mild acid (i.e., in a gastric environment). Other components that may be included in the reverse-enteric coating composition include, but are not limited to, colorants, flavors, opacifiers, and preservatives.

Enrobing and Coating Processes

Provided below is a discussion of enrobing processes and coating processes according to some embodiments. Any suitable enrobing and/or coating process may be used, and the explanations provided are just examples of such suitable processes.

Enrobing Process

Gastric residence systems may be enrobed with a coating composition using any suitable enrobing technique. Provided below are processes for coating composition preparation and enrobing, according to some embodiments.

Figure 7:
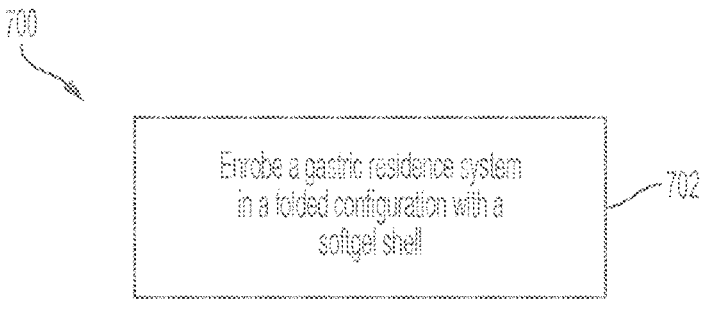
FIG. 7 shows a method of making an enrobed gastric residence dosage form, according to some embodiments.

FIG. 7 provides a schematic showing a method 700 of preparing an enrobed gastric residence dosage form, according to some embodiments.

Method 700 may include folding a gastric residence system and inserting the folded gastric residence system into a container. Folding may be performed either manually or mechanically. Folding the gastric residence system may include compacting or compressing the gastric residence system into its folded configuration. Inserting the gastric residence system into a container may include inserting the compacted gastric residence system into a sleeve, a capsule, or another container of appropriate size.

In some embodiments, methods for making an enrobed gastric residence dosage form may include receiving the foldable gastric residence system in an unfolded form. For example, the foldable gastric residence system can be received at a vibratory bowl feeder or a pick and place conveyor. In some embodiments, methods for preparing an enrobed gastric residence dosage form may include orienting the gastric residence system into a folding position. Methods may also include folding the gastric residence system into a folded configuration. Once the gastric residence dosage form is in a folded configuration, the folded gastric residence dosage form may be inserted into an opening of a container. Processes for encapsulating gastric residence systems are provided in further detail in Application PCT/US2018/051816, the entirety of which is incorporated herein.

In step 702 of the method for making an enrobed gastric residence dosage form, a gastric residence system may be enrobed with a coating. For example, a folded gastric residence system may be enrobed with a coating using a rotary die encapsulation process, such as that discussed below.

In particular, to prepare the coating composition, gelatin may be added to water and dissolved to form a gelatin solution. A plasticizer may then be added to the gelatin solution. Optionally, small amounts of opacifiers, colorants, flavors, and/or preservatives may also be added. Each component of the coating composition may be added in an amount disclosed above.

The solution can be mixed at a temperature from 60 to 100° C. or from 70 to 90° C. In some embodiments, the solution may be mixed at a temperature more than 60° C., more than 65° C., more than 70° C., more than 75° C., more than 80° C., more than 85° C., more than 90° C., or more than 95° C. In some embodiments, the solution may be mixed at a temperature less than 100° C., less than 95° C., less than 90° C., less than 85° C., less than 80° C., less than 75° C., less than 70° C., or less than 65° C.

Once the solution has been blended, it may be cooled. In some embodiments, the solution may be cooled at a temperature from 40 to 70° C. or from 50 to 60° C. In some embodiments, the solution may be cooled at a temperature more than 40° C., more than 45° C. more than 50° C., more than 55° C., more than 60° C., or more than 65° C. In some embodiments, the solution may be cooled at a temperature less than 70° C., less than 65° C., less than 60° C., less than 55° C., less than 50° C., or less than 45° C.

Once the solution has been cooled, it may be cast into ribbons. In particular, the cooled solution may be cast into ribbons by spreading onto rotating drums. As the ribbons cool further, they may be passed through rollers (e.g., oiled rollers) and fed into a rotary die enrobing process (described in detail below).

Once the ribbons are prepared, they can be used to enrobe folded gastric residence systems. In some embodiments, ribbons of gelatin-based formulation (e.g., such as the ribbons of gelatin-water-plasticizer solution described above) may be fed over counter-rotating dies. Cavities of the counter-rotating dies may represent the shape of the enrobed product. Gastric residence systems, in their folded configurations (with or without a sleeve and/or capsule), may be fed into the enrobing process from a wedge positioned above the dies. As the folded gastric residence systems are fed into the die cavities, the dies rotate to form a gelatin encasing around the folded gastric residence system. In some embodiments, the rotating dies may apply pressure and heat to join two gelatin ribbons (i.e., one from each counter-rotating die) to form a hermetic seal around the folded gastric residence system and remove any excess gelatin. The enrobed gastric residence systems may then be dropped from the bottom of the dies and fed into a tumble dryer. The enrobed gastric residence systems may be in the tumble dryer from a few minutes to several hours. After drying in the tumble dryer, the enrobed gastric residence systems may be dried at ambient conditions for a few hours to several days. For example, the enrobed gastric residence systems may be dried at ambient conditions until a desired gelatin hardness or equilibrium water content is achieved. Once dried, the gelatin surface may be polished. In some embodiments, the gelatin surface may be polished with a lubricant (e.g., lecithin).

Several processing conditions may be specified during the enrobing process. Processing conditions include at least ribbon thickness, wedge temperature, spreader box temperature, die pressure, machine speed, time in tumble dryer, dryer temperature, and dryer relative humidity.

The gelatin ribbons may vary in thickness as needed based on the size of the gastric residence system, the desired thickness of the coating, the size of the die cavities, etc. In some embodiments, ribbon thickness may be from 0.01 to 0.03 or from 0.015 to 0.025 inches in thickness. In some embodiments, the ribbons may be more than 0.01 inches, more than 0.0125 inches, more than 0.015 inches, more than 0.0175 inches, more than 0.02 inches, more than 0.0225 inches, more than 0.025 inches, or more than 0.0275 inches in thickness. In some embodiments, the ribbons may be less than 0.03 inches, less than 0.0275 inches, less than 0.025 inches, less than 0.0225 inches, less than 0.02 inches, less than 0.0175 inches, less than 0.015 inches, or less than 0.125 inches in thickness.

The temperature of the wedge may be from 85 to 100° F. In some embodiments, the temperature of the wedge may be more than 85° F., more than 88° F., more than 90° F., more than 93° F., more than 95° F., or more than 98° F. In some embodiments, the temperature of the wedge may be less than 100° F., less than 98° F., less than 95° F., less than 93° F., less than 90° F., or less than 88° F.

In some embodiments, the temperature of the spreader box may be from 120 to 150° F. In some embodiments, the temperature of the spreader box may be more than 120° F., more than 125° F., more than 130° F., more than 135° F., more than 140° F., or more than 145° F. In some embodiments, the temperature of the spreader box may be less than 150° F., less than 145° F., less than 140° F., less than 135° F., less than 130° F., or less than 125° F.

In some embodiments, the die pressure of the rotating dies may be from 60 to 100 pounds per square inch (psi). In some embodiments, the die pressure may be more than 60 psi, more than 65 psi, more than 70 psi, more than 75 psi, more than 80 psi, more than 85 psi, more than 90 psi, or more than 95 psi.

The speed of the enrobing machine (e.g., rotary die encapsulator) may be optimized. In some embodiments, the speed may be from 0.5 to 5.0 rpm or from 1.0 to 4.0 rpm. In some embodiments, the speed may be more than 0.5 rpm, more than 1.0 rpm, more than 1.5 rpm, more than 2.0 rpm, more than 2.5 rpm, more than 3.0 rpm, more than 3.5 rpm, more than 4.0 rpm, or more than 4.5 rpm. In some embodiments, the speed may be less than 5.0 rpm, less than 4.5 rpm, less than 4.0 rpm, less than 3.5 rpm, less than 3.0 rpm, less than 2.5 rpm, less than 2.0 rpm, less than 1.5 rpm, or less than 1.0 rpm.

As mentioned above, the enrobed gastric residence system may reside in the tumble dryer for an amount of time that may depend upon the coating formulation, the amount of coating material, the size of the enrobed gastric residence dosage form, etc. In some embodiments, the enrobed gastric residence dosage form may reside in the tumble dryer from 5 to 60 minutes or from 10 to 30 minutes. In some embodiments, the enrobed gastric residence dosage form may reside in the tumble dryer for more than 5 minutes, more than 10 minutes, more than 15 minutes, more than 20 minutes, more than 25 minutes, more than 30 minutes, more than 40 minutes, or more than 50 minutes. In some embodiments, the enrobed gastric residence dosage form may reside in the tumble dryer for less than 60 minutes, less than 50 minutes, less than 40 minutes, less than 30 minutes, less than 25 minutes, less than 20 minutes, less than 15 minutes, or less than 10 minutes.

The dryer temperature may be from 15° C. to 50° C. In some embodiments, the dryer temperature may be more than 15° C., more than 20° C., more than 25° C., more than 30° C., more than 35° C., more than 40° C. or more than 45° C. In some embodiments, the dryer temperature may be less than 50° C., less than 45° C., less than 40° C., less than 35° C., less than 30° C., less than 25° C., or less than 20° C.

The dryer relative humidity may be from 5 to 40% or from 10 to 30%. In some embodiments, the dryer relative humidity may be more than 5%, more than 10%, more than 15%, more than 20%, more than 25%, more than 30%, or more than 35%. In some embodiments, the dryer relative humidity may be less than 40%, less than 35%, less than 30%, less than 25%, less than 20%, less than 15%, or less than 10%.

Coating Process

In some embodiments, an enrobed gastric residence dosage form may be coated with a reverse-enteric coating designed to modify gastric residence system deployment behavior and surface properties of the enrobed gastric residence dosage form.

For example, a pan-coating process may be used to coat the enrobed gastric residence dosage forms. In some embodiments, an LDCS 48098/Freund-Vector pan coater may be used with a 1.5 L pan size, a SCHLICK ABC LDCS-FP HCC-6869-3 spray gun, and peroxide-cured silicone pump tubing to coat the encapsulated gastric residence systems.

Several processing conditions may be specified during the pan-coating process. Processing conditions include at least inlet temperature, exhaust temperature, coater airflow, pan speed, pump speed, atomization pressure, pattern pressure, spray rate, drying pan speed, and drying time in pan. For example, the inlet temperature may be from 30 to 70° C., from 35 to 65° C., or from 40 to 60° C. In some embodiments, the inlet temperature may be less than 70° C., less than 65° C., less than 60° C., less than 55° C., less than 50° C., or less than 45° C. In some embodiments, the inlet temperature may be more than 30° C., more than 35° C., more than 40° C., more than 45° C., or more than 50° C.

The exhaust temperature may be from 20° C. to 60° C., from 25° C. to 50° C., or from 30 to 40° C. In some embodiments, the exhaust temperature may be less than 60° C., less than 50° C., less than 40° C., or less than 30° C. In some embodiments, the exhaust temperature may be more than 20° C., more than 30° C., more than 40° C., or more than 50° C.

The coater airflow may be from 20 to 80 cubic feet per minute (CFM), from 30 to 70 CFM, or from 40 to 60 CFM. In some embodiments, the coater airflow may be less than 80 CFM, less than 70 CFM, less than 60 CFM, less than 50 CFM, or less than 40 CFM. In some embodiments, the coater airflow may be more than 20 CFM, more than 30 CFM, more than 40 CFM, more than 50 CFM, or more than 60 CFM.

The pan speed may be from 10 to 50 rpm, from 15 to 40 rpm, or from 20 to 30 rpm. In some embodiments, the pan speed may be more than 10 rpm, more than 15 rpm, more than 20 rpm, more than 30 rpm, or more than 40 rpm. In some embodiments, the pan speed may be less than 50 rpm, less than 40 rpm, less than 30 rpm, less than 20 rpm, or less than 15 rpm.

The pump speed may be from 2 to 15 rpm, from 3 to 12 rpm, or from 5 to 10 rpm. In some embodiments, the pump speed may be more than 2 rpm, more than 3 rpm, more than 5 rpm, or more than 10 rpm. In some embodiments, the pump speed may be less than 15 rpm, less than 12 rpm, less than 10 rpm, or less than 5 rpm.

The atomization pressure may be from 10 to 40 pounds per square inch (psi), from 15 to 35 psi, or from 20 to 30 psi. In some embodiments, the atomization pressure may be more than 10 psi, more than 15 psi, more than 20 psi, or more than 25 psi. In some embodiments, the atomization pressure may be less than 40 psi, less than 35 psi, less than 30 psi, less than 25 psi, or less than 20 psi.

The pattern pressure may be from 10 to 40 psi, from 15 to 35 psi, or from 20 to 30 psi. In some embodiments, the pattern pressure may be more than 10 psi, more than 15 psi, more than 20 psi, or more than 25 psi. In some embodiments, the pattern pressure may be less than 40 psi, less than 35 psi, less than 30 psi, less than 25 psi, or less than 20 psi.

The spray rate may be from 1 to 10 grams per minute (g/min) or from 3 to 8 g/min. In some embodiments, the spray rate may be more than 1 g/min, more than 2 g/min, more than 3 g/min, more than 4 g/min, or more than 5 g/min. In some embodiments, the spray rate may be less than 10 g/min. less than 8 g/min, less than 6 g/min, less than 5 g/min, or less than 4 g/min.

The drying pan speed may be from 1 to 30 rpm, from 3 to 20 rpm, or from 5 to 10 rpm. In some embodiments, the drying pan speed may be more than 1 rpm, more than 2 rpm, more than 3 rpm, more than 4 rpm, more than 5 rpm, more than 8 rpm, more than 10 rpm, or more than 15 rpm. In some embodiments, the dying pan speed may be less than 30 rpm, less than 25 rpm, less than 20 rpm, less than 15 rpm, less than 10 rpm, less than 8 rpm, or less than 5 rpm.

The total drying time in pan may be from 15 to 120 minutes, from 30 to 100 minutes, or from 45 to 80 minutes. In some embodiments, the total drying time in pan may be more than 15 minutes, more than 30 minutes, more than 45 minutes, more than 60 minutes, or more than 80 minutes. In some embodiments, the total drying time in pan may be less than 120 minutes, less than 100 minutes, less than 80 minutes, less than 60 minutes, or less than 45 minutes. In some embodiments, the drying time may be continuous. In some embodiments, the drying time may be discontinuous.

EXAMPLES

Figure 8:
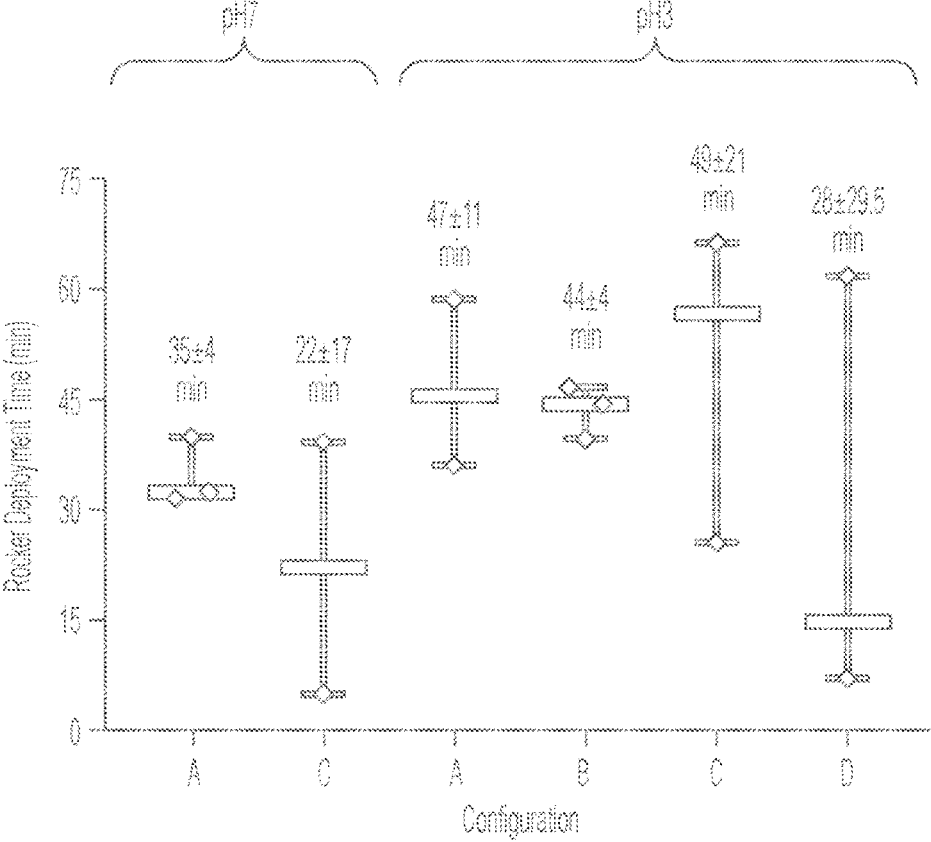
FIG. 8 provides deployment time data for different types of sleeves and capsules in enrobed gastric residence dosage forms, according to some embodiments.

Example 1: The deployment time was tested for various types of sleeves and capsules. The specific capsules and sleeves are shown in Table 1, below. The data is provided in FIG. 8. As shown in the Table, four different combinations of sleeve and capsule types were tested. As shown. Groups A and C were tested at pH 7, and Groups A. B, C, and D were tested at pH 3. As shown, Groups C and D exhibited less consistent deployment times. Thus, using a capsule (e.g., as in Groups A and B) may help control the thickness of the enrobed coating layer such that it is consistent. A consistent enrobed coating layer may result in more predictable deployment times.

Figure 9:
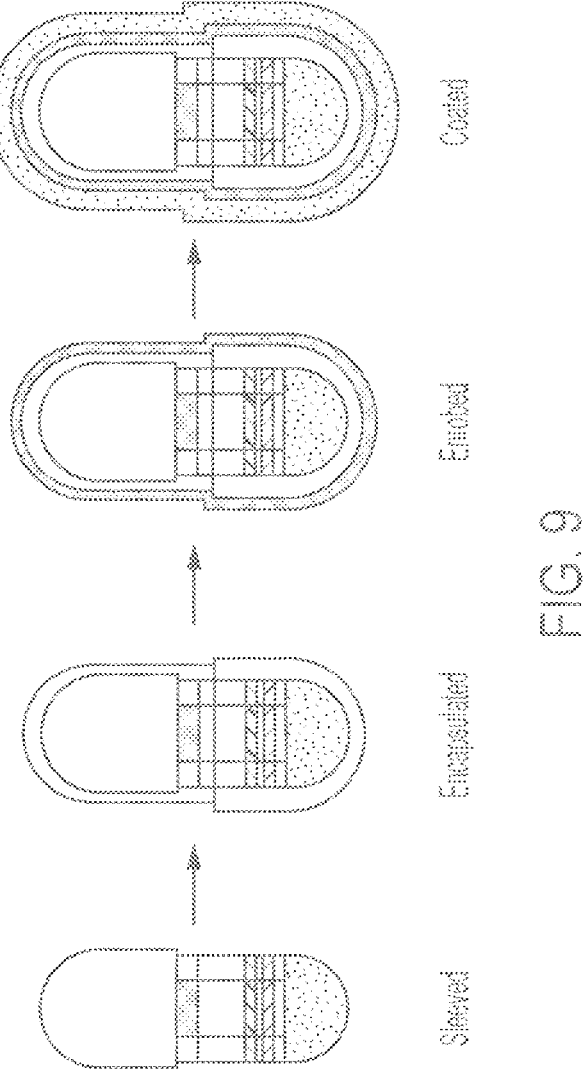
FIG. 9 shows the process flow from sleeving, encapsulation, enrobing and coating, according to some embodiments.

The enrobed gastric residence systems from Group B (Vcaps® Primary sleeve and VCaps® Primary capsule) were coated with a reverse-enteric coating using a pan coating process. The coating formulation comprised the reverse-enteric polymer Eudragit E (90.7% w/w), dibutyl sebacate (4.65% w/w) and magnesium stearate (4.65% w/w). Dibutyl sebacate was added as a plasticizer and magnesium stearate was used as an anti-tacking agent. The coat weights ranged from 31.5 to 34.5 mg. The schematic in FIG. 9 describes the process flow from sleeving, encapsulation, enrobing and coating.

Figure 10:
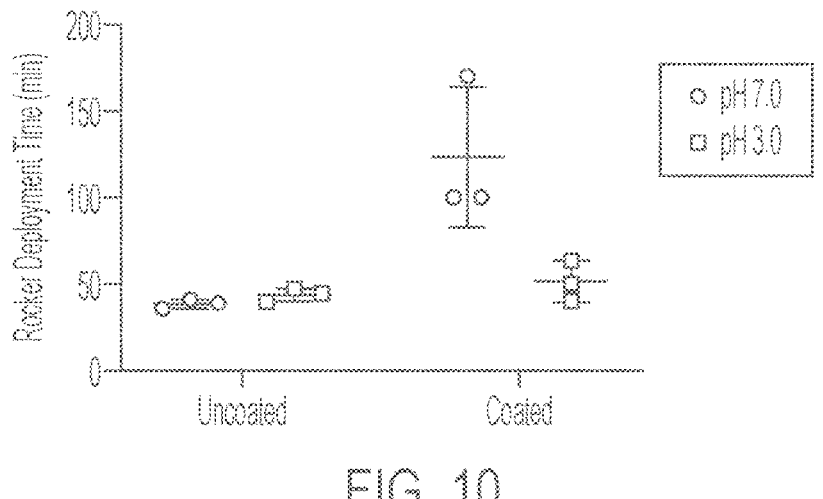
FIG. 10 shows deployment times of uncoated and coated enrobed stellates.

The deployment time of coated enrobed gastric residence systems was evaluated at pH 7 (to mimic esophageal conditions) and at pH 3 (to simulate weak gastric conditions) using the Deployment Test described in detail below. FIG. 10 shows the deployment times of uncoated and coated capsules. The data indicates that the coating formulation delays capsule opening at esophageal pH and makes the enrobed gastric residence system pH responsive.

TABLE 1

| Capsule and Sleeve combinations tested. | | | | |
|---|---|---|---|---|
| Group | A | B | C | D |
| Capsule Type | 00EL VCaps ® Primary | 00EL VCaps ® Primary | No capsule | No capsule |
| Sleeve Type | 0EL VCaps ® Plus | 0EL VCaps ® Primary | 0EL VCaps ® Plus | 0EL VCaps ® Primary |

Additionally, a static coefficient of friction (CoF) analysis on a hydrated collagen surface was performed on uncoated and coated enrobed gastric residence systems. The CoF for uncoated enrobed gastric residence systems with exposed gelatin shell was $0.7 \pm 0.1$, whereas the CoF for coated enrobed gastric residence systems with no gelatin exposed on surface was $0.09 \pm 0.02$. This data indicates that coating enrobed gastric residence systems with a formulation containing magnesium stearate as an anti-tacking agent in combination with Eudragit E and dibutyl sebacate may be optimal for reducing friction.

Example 2: Two types of gelatin shell formulations were evaluated for enrobing stellates. The components of the two formulations are provided in Table 2, below. The key difference in the two formulations was their bloom strength and the presence of a low molecular weight (3-6 kD) gelatin hydrolysate. The low molecular weight gelatin hydrolysate can allow faster hydration. Prior to enrobing, gastric residence systems were folded/encapsulated in four different capsule and sleeve configurations shown in Table 3, below. Enrobing was performed on each of the folded configurations for both gelatin formulations.

TABLE 2

| Two gelatin shell formulations used for enrobing gastric residence systems. | | |
|---|---|---|
| Reagent | Formulation 1 (APP073119) | Formulation 2 (APP072619) |
| 150 Bloom Lime Bone Gelatin | present | N/A |
| 115 Bloom Lime Bone Gelatin RXL R^2 | N/A | present |
| Gelatin Hydrolysate | present | N/A |
| Glycerin, USP | present | present |
| Purified Water | present | present |
| Expected Bloom (g) | 150-170 | 92-138 |

TABLE 3

| Configurations of folded gastric residence system. Sz 00EL VCaps Plus Capsule, Sz 0 VCaps Plus Sleeve. | |
|---|---|
| Sublot | Folded Gastric Residence System Configuration (encapsulation) |
| A | 1 sleeve (arm-side), with capsule |
| B | No sleeve, with capsule |
| C | 1 sleeve (arm-side), no capsule |
| D | 2 sleeves (arm- & core-side), no capsule |

The enrobed gastric residence systems were evaluated for appearance, dimension, and deployment timing at pH 3 (to simulate deployment in weak gastric pH conditions). FIG.

11 shows the uncoated deployment times for both enrobing formulations. No significant difference was observed between the two formulations in terms of appearance and dimensions. No significant difference in deployment times at pH 3 for Sublots A & B. However, the deployment times at pH 3 for Sublots C & D have higher variability for Formulation 1 with the hydrolysate compared to Formulation 2. Sublot C enrobed gastric residence systems exhibit the fastest deployment times for both formulations. All uncoated enrobed stellates deployed in less than 60 mins at pH 3, except one in Formulation 1—Sublot D. Sublot D took 85 mins to deploy at pH 3.

The deployment time of Sublot C enrobed gastric residence systems was also evaluated at pH 7, which simulates esophageal environment, to assess the pH responsiveness of the enrobing formulations. For both formulations, there was no significant impact of pH on deployment time.

Figures 11, 12:
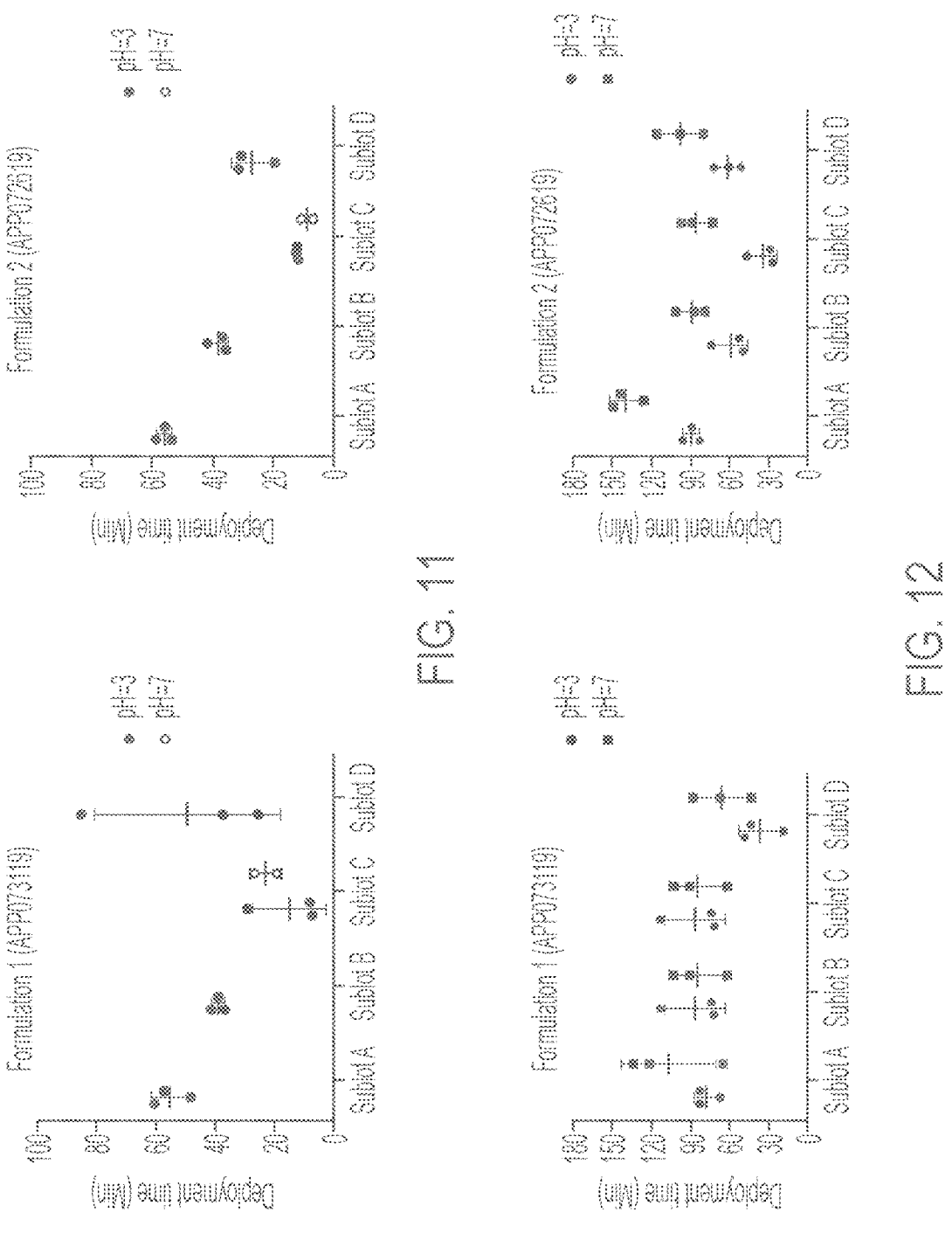
FIG. 11 shows the uncoated deployment times for two enrobing formulations.
FIG. 12 shows deployment times at both pH 3 & pH 7 for the two enrobing formulations also depicted in FIG. 9.

Gastric residence systems enrobed with both formulations were then coated with an Eudragit E based pH responsive coating. The processability, appearance and deployment times of the coated enrobed gastric residence systems were assessed (as shown in FIG. 12 & Table 4). Gastric residence systems enrobed with the hydrolysate containing formulation 1 showed cracks in the shell after the pan-coating process. Formulation 2 enrobed gastric residence systems did not show any cracking and had slightly higher coating weight gain indicating better coating adherence.

FIG. 12 shows the deployment times at both pH 3 & pH 7 for both enrobing formulations. Formulation 1 enrobed gastric residence systems don't show pH responsive behavior for Sublots A, B & C post-coating. However, coated enrobed gastric residence systems with Formulation 2 show pH responsive behavior for all Sublots.

For example, in case of Formulation 2 Subplot C, the average deployment time is 36±11 min at pH 3 and 87±12 min at pH 7. This provides a two-fold differential in deployment time at pH 7 compared to pH 3 for this group of gastric residence systems. Such a pH responsive behavior of coated enrobed gastric residence systems can provide sufficient delay at esophageal pH while allowing rapid deployment in the gastric environment.

TABLE 4

Pan-coating processability observations of enrobed gastric residence systems.

| | Enrobing Formulation | | | | | | | |
| | 1 (APP07319) | | | | 2 (APP072619) | | | |
| | Sublot | | | | | | | |
| | A | B | C | D | A | B | C | D |
| Coating Weight Gain (mg) | 33.5 | 32.5 | 26.8 | 25.3 | 35.6 | 36.8 | 29.3 | 30 |
| Appearance after coating | Good | Good | cracks in shell | cracks in shell | Good | Good | Good | Good |

Figure 13A:
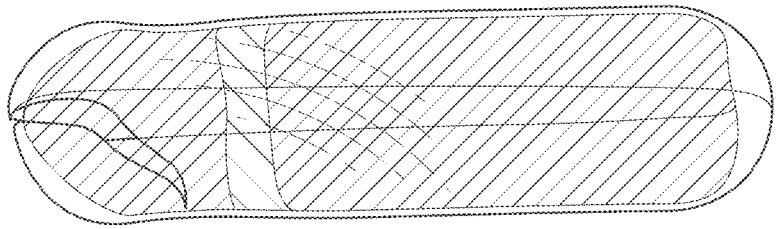
FIG. 13A shows a cracked enrobed gastric residence system after coating, according to some embodiments.
Figure 13B:
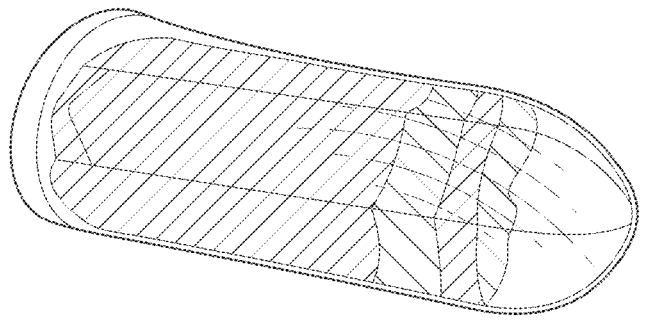
FIG. 13B shows an enrobed gastric residence system without being encapsulated with a capsule, according to some embodiments.
Figure 13C:
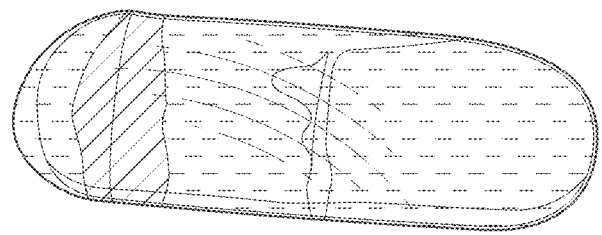
FIG. 13C shows an enrobed gastric residence system that encapsulated with a capsule, according to some embodiments.

FIGS. 13A-C show various images of enrobed gastric residence systems from this trial. Specifically, FIG. 13A shows a cracked enrobed gastric residence system after coating. FIG. 13B shows an enrobed gastric residence system without being encapsulated with a capsule. FIG. 13C shows an enrobed gastric residence system that encapsulated with a capsule.

Example 3: Two different anti-tacking agents, talc and magnesium stearate, were tested for static coefficient of friction and deployment time. Twenty two weight-percent talc to total solids was used and 4.6 wt. % magnesium stearate to total solids was used. The reverse-enteric, low-friction static coefficient polymers tested may help increase slipperiness of a dosage form when used to coat the capsule. A more slippery dosage form can help minimize the risk of pill esophagitis. The testing was performed according to the techniques discussed in detail further below.

Further, the static coefficient of friction at two minutes for uncoated VCaps Plus HPMC capsule was 0.35±0.04. However, the static coefficient of friction of VCaps® Plus HPMC capsule coated with a formulation containing Eudragit E, dibutyl sebacate and magnesium stearate was 0.06±0.01. This data indicates that a reverse-enteric coating of Eudragit E in presence of magnesium stearate and dibutyl sebacate is efficient in reducing friction during swallowing of an HPMC capsule.

Figure 14:
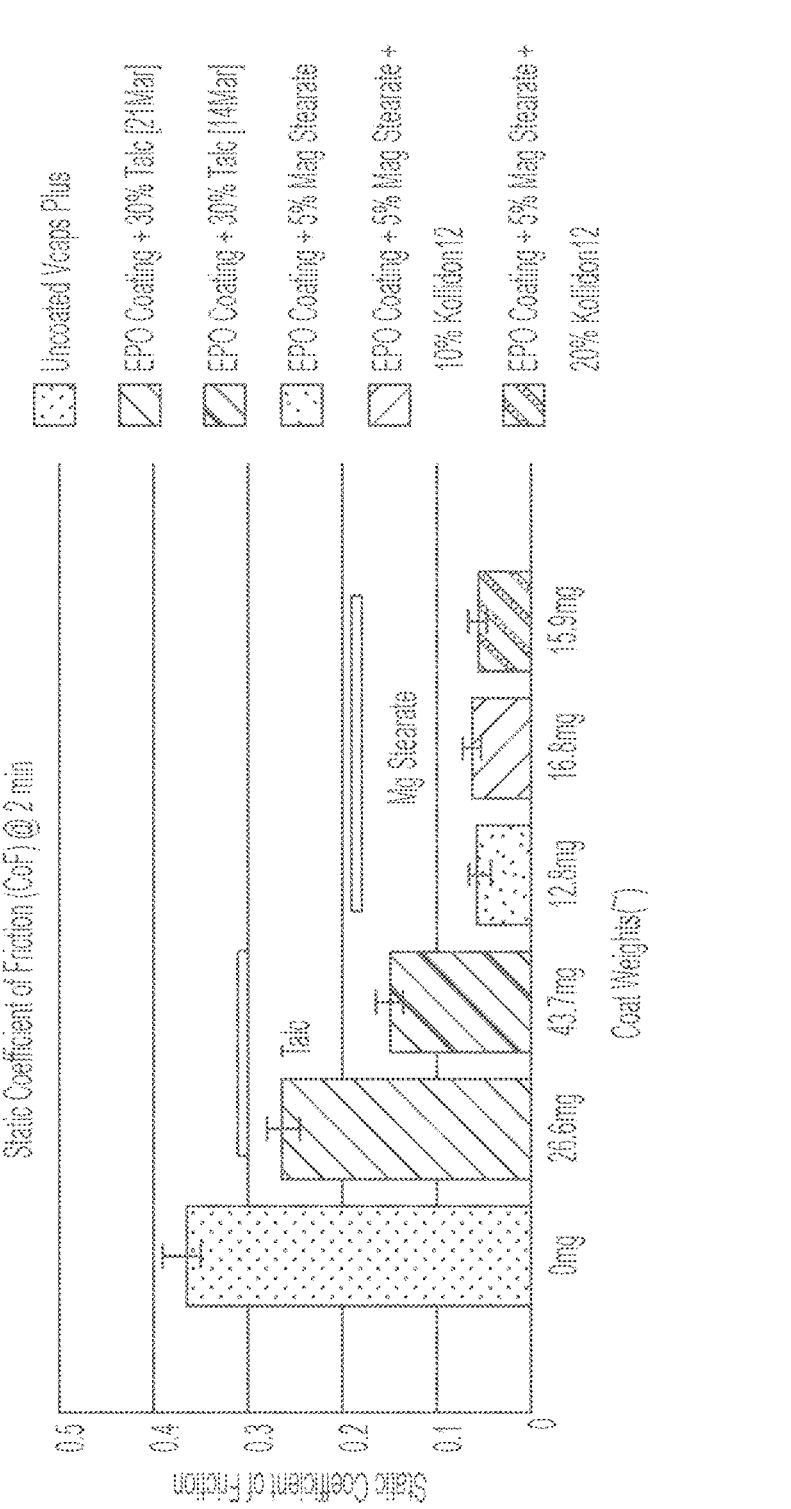
FIG. 14 shows static coefficient of friction data for different coating formulations, according to some embodiments.

As shown in FIG. 14, both the dosage forms having the talc coating and the dosage forms having the magnesium stearate coating have lower static coefficients of friction than the uncoated dosage form, indicating that both talc and magnesium stearate help make the dosage form easier to swallow. Below, in Table 5, the results show that both the talc-comprising coating and the magnesium stearate-comprising coating yield acceptable deployment times in both a weakly acidic gastric environment (i.e., 3.0 pH) and an esophageal environment (i.e., pH 7.0).

TABLE 5

Deployment time of coated gastric residence dosage forms including either talc or magnesium stearate.

| Deployment Time (min) | pH 3.0 | pH 7.0 |
|---|---|---|
| Talc coating (23 mg) | 20.5 ± 2.1 min | 75 ± 11 min |
| Mg Stearate coating (13 mg) | 16.9 ± 2.6 min | 58.7 ± 11.3 mm |

Figure 15:
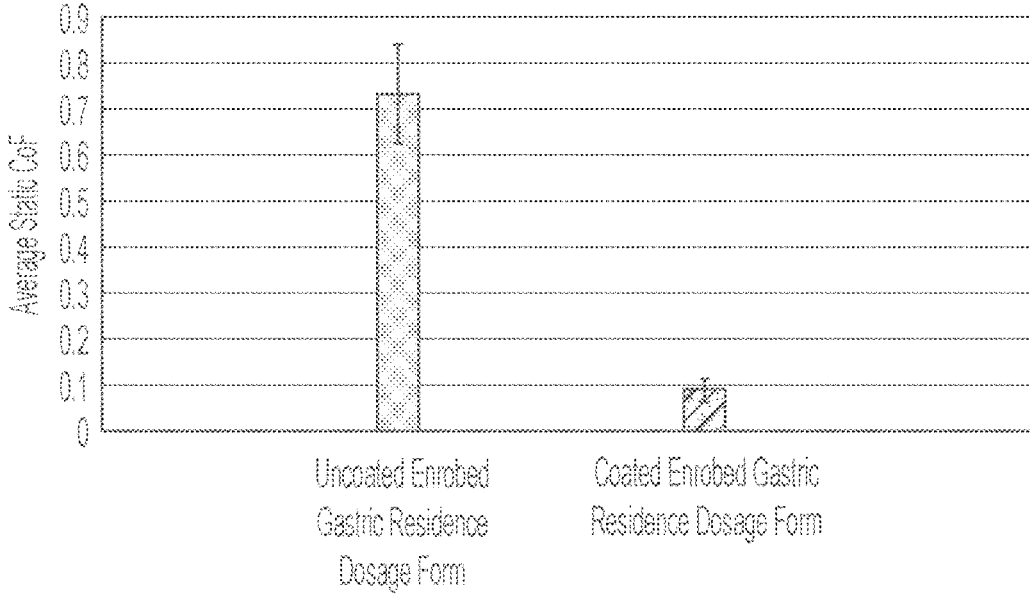
FIG. 15 shows static coefficient of friction testing data for uncoated and coated enrobed gastric residence dosage forms, according to some embodiments.

Example 4: Uncoated and coated enrobed gastric residence systems were tested for static coefficient of friction. As shown in FIG. 15, the difference between the static coefficient of friction of the coated enrobed gastric residence dosage forms and the static coefficient of friction of the uncoated enrobed gastric residence dosage forms is significant. Both dosage forms include enrobed gastric residence dosage forms according to embodiments described herein. However, the coated enrobed gastric residence dosage forms include a coating layer surrounding the enrobed gastric residence dosage form. The coating formulation of the coated enrobed gastric residence dosage forms comprises Eudragit E (90.7% w/w), dibutyl sebacate (4.65% w/w) and magnesium stearate (4.65% w/w). As shown, this coating can reduce the static coefficient of friction of an enrobed gastric residence dosage form by 85% or more (i.e., $$\frac{\text{static coefficient of friction of coated enrobed gastric residence dosage form}}{\text{static coefficient of friction of uncoated enrobed gastric residence dosage form}}$$

is less than or equal to 0.15).

Testing Methods

Deployment Test: To measure deployment time, enrobed gastric residence dosage forms can be placed in 35 mL if the specified media on a laboratory rocker. Specifically, a 450 mL jar comprising an 80 mm diameter, a 94 mm height, and a polytetrafluoroethylene-lined lid was used. Once the enrobed gastric residence dosage form was placed into the jar with the 35 mL media, the jar was sealed, inverted, and immediately placed on the laboratory rocker. The laboratory rocker was set at 30 cycles per minute.

Various media were used depending on the testing conditions desired. In some tests, a phosphate buffered saline solution was used at either a pH of 7.0 (to replicate a human esophageal pH condition) or a pH of 3.0 (to replicate a human gastric weak acidic pH condition). The 7.0 pH solution was prepared by dissolving 1.36 grams of monobasic potassium phosphate, anhydrous, and 8.41 grams of sodium chloride in water and adjusting to pH 7.0 with sodium hydroxide, then diluting to a final volume of 1.0 liters with water. The 3.0 pH solution was prepared by dissolving 1.36 grams of monobasic potassium phosphate, anhydrous, and 8.41 grams of sodium chloride in water and adjusting to pH 3.0 with hydrochloric acid, then diluting to a final volume of 1.0 liters with water.

Deployment tests were also conducted using a media of hydrochloric acid (pH 1.5) with sodium chloride to replicate a human gastric strong acidic pH condition. This solution was prepared by dissolving 9.00 grams of sodium chloride in a solution of 1.5 pH hydrochloric acid to a final volume of 1.0 liters.

Figure 16A:
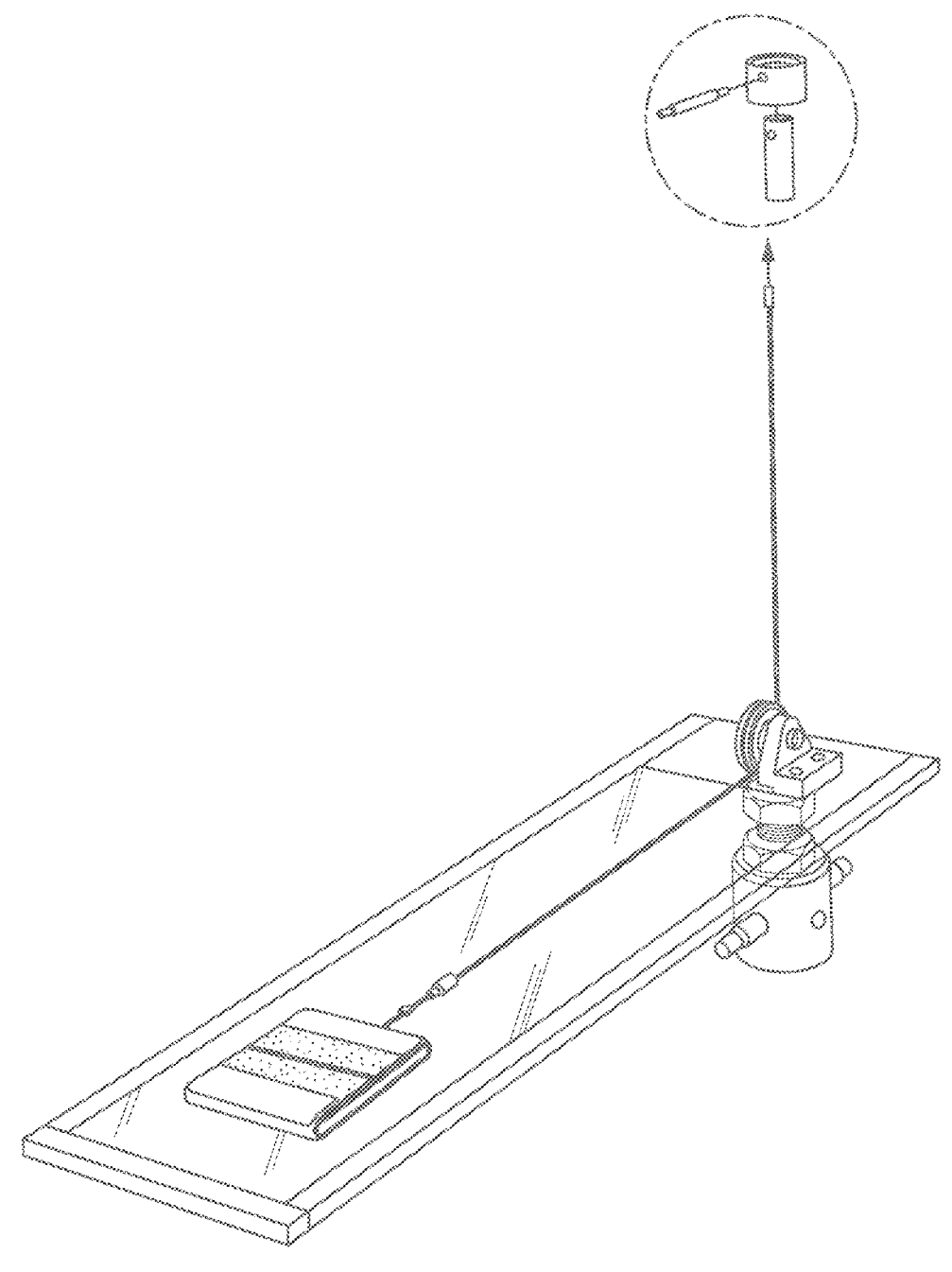
FIG. 16A shows an Instron testing tool as used to test deployment time, according to some embodiments.
Figure 16B:
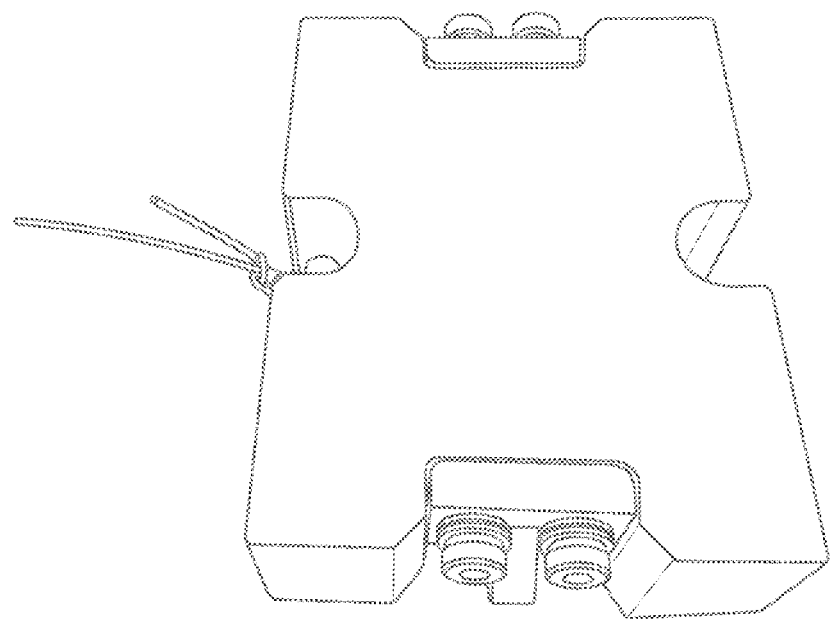
FIG. 16B shows a view of a custom sled for testing static coefficient of friction, according to some embodiments.
Figure 16C:
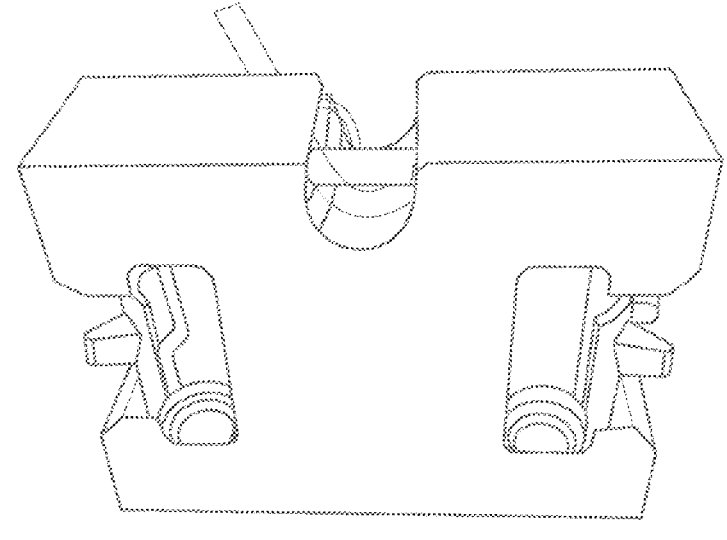
FIG. 16C shows a view of a custom sled for testing static coefficient of friction, according to some embodiments.

Friction Test: Squares of approximate three inches by three inches were cut from sausage casing (LEM products Smoked Clear Edible Collagen Casing) and soaked in deionized water for at least 30 minutes. One square was cut for each sample to be tested. An Instron tensile testing machine (Model 3342), shown in FIG. 16A, was used with the static coefficient of friction fixture (standard add-on) and a 10 N load cell. A custom sled was used to hold two capsules oriented horizontally in direct contact with the casing surface. FIGS. 16B and 16C show the custom sled.

For each capsule sample, a hydrated casing square was laid on the testing surface and flattened by wiping with a rubber scraper from the center to each edge to remove any air bubbles and excess liquid located between the casing and the testing surface. Two capsule samples were inserted into the slots on the custom machined sled. The sled was attached to a nylon cord. The cord was passed through the fixture pulley and up to the hook on the 10 N load cell attached to the Instron crosshead. The sled was placed down on the casing, with only the two capsules contacting the casing, in an orientation such that the direction of movement as axial with respect to the capsules. The sled was let rest in place for a specified amount of time. Generally, the sled was let to rest in place for times from 2 to 10 minutes, to reflect various swallowing times.

At the end of the hold time, the crosshead was caused to move upward at a speed of 150 mm/min, pulling the sled forward on the testing surface until a travel distance of 15 mm was reached. The peak force which brought the sled in to motion was measured. The static coefficient of friction for each pair of capsules was calculated by dividing the peak force by the normal force exerted by gravity on the sled and capsules (the normal force exerted by gravity on the sled and capsules was determined based on sled and capsule weight). The static coefficients of friction for each capsule group were averaged and compared.

EMBODIMENTS

The invention is further described by the following embodiments. The features of each of the embodiments are combinable with any of the other embodiments where appropriate and practical.

Embodiment 1. An enrobed gastric residence dosage form comprising: a gastric residence system in a folded configuration; and a coating enrobing the gastric residence system in the folded configuration, wherein the enrobed gastric residence dosage form is configured to release the gastric residence system in a stomach of a patient, allowing the gastric residence system to assume an open configuration.

Embodiment 2. The enrobed gastric residence dosage form of embodiment 1, wherein a thickness of the coating enrobing the gastric residence system in the folded configuration is from 50 to 250 microns.

Embodiment 3. The enrobed gastric residence dosage form of embodiment 1 or 2, wherein the coating enrobing the gastric residence system in the folded configuration is applied to the gastric residence system in the folded configuration using a rotary die encapsulation process.

Embodiment 4. The enrobed gastric residence dosage form of any of embodiments 1-3, wherein the coating enrobing the gastric residence system in the folded configuration comprises a softgel type shell material.

Embodiment 5. The enrobed gastric residence dosage form of any of embodiments 1-4, wherein the coating enrobing the gastric residence system in the folded configuration provides a hermetic seal.

Embodiment 6. The enrobed gastric residence dosage form of any of embodiments 1-5, wherein the coating enrobing the gastric residence system in the folded configuration comprises water, a plasticizer, and a gelling agent.

Embodiment 7. The enrobed gastric residence dosage form of embodiment 6, wherein the coating enrobing the gastric residence system in the folded configuration comprises from 5 to 10 wt. % water.

Embodiment 8. The enrobed gastric residence dosage form of embodiment 6 or 7, wherein the plasticizer comprises one or more of glycerin or sorbitol.

Embodiment 9. The enrobed gastric residence dosage form of any of embodiments 6-8, wherein the coating enrobing the gastric residence system in the folded configuration comprises from 20 to 60 wt. % plasticizer.

Embodiment 10. The enrobed gastric residence dosage form of any of embodiments 6-9, wherein the gelling agent is one or more of gelatin, pullulan, hydroxypropyl methylcellulose, or potato starch.

Embodiment 11. The enrobed gastric residence dosage form of any of embodiments 6-10, wherein the coating enrobing the gastric residence system in the folded configuration comprises from 35 to 75 wt. % gelling agent.

Embodiment 12. The enrobed gastric residence dosage form of any of embodiments 1-11, wherein the coating enrobing the gastric residence system in the folded configuration comprises a polymer.

Embodiment 13. The enrobed gastric residence dosage form of embodiment 12, wherein the polymer comprises a polymethacrylate-based polymer.

Embodiment 14. The enrobed gastric residence dosage form of embodiment 12 or 13, wherein the coating enrobing the gastric residence system in the folded configuration comprises from 10 to 50 wt. % polymer.

Embodiment 15. The enrobed gastric residence dosage form of any of embodiments 1-14, comprising a sleeve, wherein the sleeve surrounds at least a portion of the gastric residence system in the folded configuration.

Embodiment 16. The enrobed gastric residence dosage form of embodiment 15, wherein the sleeve comprises at least one of gelatin, hydroxypropyl methylcellulose, or pullulan.

Embodiment 17. The enrobed gastric residence dosage form of any of embodiments 1-16, comprising a capsule encapsulating the gastric residence system in the folded configuration.

Embodiment 18. The enrobed gastric residence dosage form of embodiment 17, wherein the capsule comprises at least one of gelatin, hydroxypropyl methylcellulose, or pullulan.

Embodiment 19. The enrobed gastric residence dosage form of any of embodiments 1-18, comprising a coating on the coating enrobing the gastric residence system in the folded configuration.

Embodiment 20. The enrobed gastric residence dosage form of embodiment 19, wherein the coating on the coating enrobing the gastric residence system comprises a reverse-enteric polymer.

Embodiment 21. The enrobed gastric residence dosage form of embodiment 20, wherein the reverse-enteric polymer comprises a polymethacrylate-based polymer.

Embodiment 22. The enrobed gastric residence dosage form of any of embodiments 19-21, wherein the coating on the coating enrobing the gastric residence system comprises an anti-tacking agent.

Embodiment 23. The enrobed gastric residence dosage form of embodiment 19, wherein the anti-tacking agent comprises at least one of talc or magnesium stearate.

Embodiment 24. The enrobed gastric residence dosage form of any of embodiments 19-23, wherein the coating on the coating enrobing the gastric residence system comprises a plasticizer.

Embodiment 25. The enrobed gastric residence dosage form of embodiment 24, wherein the plasticizer comprises at least one of a phthalate, a phosphate, a citrate, a tartrate, an adipate, a sebacate, a sulfonamide, a succinate, a glycolate, a glycerolate, a benzoate, a myristate, a halogenated phenyl, or a poloxamer.

Embodiment 26. The enrobed gastric residence dosage form of embodiment 24 or 25, wherein the plasticizer comprises at least one of triacetin or dibutyl sebacate.

Embodiment 27. The enrobed gastric residence dosage form of any of embodiments 19-26, wherein the coating on the coating enrobing the gastric residence system comprises a hydration aid.

Embodiment 28. The enrobed gastric residence dosage form of embodiment 27, wherein the hydration aid comprises at least one of a polyvinylpyrrolidone, a vinylpyrrolidone-vinyl acetate copolymer, a polyethylene glycol, mannitol, or hydroxypropyl methylcellulose.

Embodiment 29. The enrobed gastric residence dosage form of any of embodiments 1-28, wherein the enrobed gastric residence dosage form allows the gastric residence system in the folded configuration to assume an open configuration in at least 20 minutes when exposed to an aqueous pH 7.0 environment.

Embodiment 30. The enrobed gastric residence dosage form of any of embodiments 1-29, wherein the enrobed gastric residence dosage form allows the gastric residence system in the folded configuration to assume an open configuration in at least 30 minutes when exposed to an aqueous pH 7.0 environment.

Embodiment 31. The enrobed gastric residence dosage form of any of embodiments 1-30, wherein the enrobed gastric residence dosage form allows the gastric residence system in the folded configuration to assume an open configuration in less than 20 minutes when exposed to an aqueous pH 3.0 environment.

Embodiment 32. The enrobed gastric residence dosage form of any of embodiments 1-31, wherein the enrobed gastric residence dosage form allows the gastric residence system in the folded configuration to assume an open configuration in less than 15 minutes when exposed to an aqueous pH 3.0 environment.

Embodiment 33. The enrobed gastric residence dosage form of any of embodiments 1-32, wherein the enrobed gastric residence dosage form is used to treat a patient.

Embodiment 34. The enrobed gastric residence dosage form of embodiment 33, wherein the patient is a human.

Embodiment 35. A coating for enrobing a gastric residence system, the coating comprising: 5-10 wt. % water; 20-60 wt. % plasticizer; and 35-75 wt. % gelling agent.

Embodiment 36. The coating of embodiment 35, wherein the coating is configured to enrobe a gastric residence system in a folded configuration to form an enrobed gastric residence dosage form, and the enrobed gastric residence dosage form is configured to release the gastric residence system in the folded configuration in a stomach of a patient, allowing the gastric residence system in the folded configuration to assume an open configuration.

Embodiment 37. The coating of embodiment 36, wherein a thickness of the coating of the enrobed gastric residence dosage form is from 50 to 250 microns.

Embodiment 38. The coating of embodiment 36 or 37, wherein the coating of the enrobed gastric residence dosage form is applied to the gastric residence system in the folded configuration using a rotary die encapsulation process.

Embodiment 39. The coating of any of embodiments 36-38, wherein the coating of the enrobed gastric residence dosage form comprises a softgel type shell material.

Embodiment 40. The coating of any of embodiments 36-39, wherein the coating of the enrobed gastric residence dosage form provides a hermetic seal.

Embodiment 41. The coating of embodiment 36-40, wherein the enrobed gastric residence dosage form allows the gastric residence system in the folded configuration to assume the open configuration in at least 20 minutes when exposed to an aqueous pH 7.0 environment.

Embodiment 42. The coating of embodiment 36-41, wherein the enrobed gastric residence dosage form allows the gastric residence system in the folded configuration to assume the open configuration in at least 30 minutes when exposed to an aqueous pH 7.0 environment.

Embodiment 43. The coating of any of embodiments 36-42, wherein the enrobed gastric residence dosage form allows the gastric residence system in the folded configuration to assume the open configuration in less than 20 minutes when exposed to an aqueous pH 3.0 environment.

Embodiment 44. The coating of any of embodiments 36-43, wherein the enrobed gastric residence dosage form allows the gastric residence system in the folded configuration to assume the open configuration in less than 15 minutes when exposed to an aqueous pH 3.0 environment.

Embodiment 45. The coating of any of embodiments 35-44, wherein the plasticizer comprises at least one of glycerin or sorbitol.

Embodiment 46. The coating of any of embodiments 35-45, wherein the gelling agent is one or more of gelatin, pullulan, hydroxypropyl methylcellulose, or potato starch.

Embodiment 47. The coating of any of embodiments 35-46, comprising a polymer.

Embodiment 48. The coating of embodiment 47, wherein the polymer comprises a polymethacrylate-based polymer.

Embodiment 49. The coating of embodiment 47 or 48, comprising from 10 to 50 wt. % polymer.

Embodiment 50. An enrobed gastric residence dosage form comprising the coating for enrobing a gastric residence system of any of embodiments 35-47, wherein the enrobed gastric residence dosage form is used to treat a patient.

Embodiment 51. The enrobed gastric residence dosage form of embodiment 50, wherein the patient is a human.

Embodiment 52. A method of making an enrobed gastric residence dosage form comprising: enrobing a gastric residence system in a folded configuration with a coating to form an enrobed gastric residence dosage form.

Embodiment 53. The method of embodiment 52, wherein the enrobed gastric residence dosage form is configured to release the gastric residence system in the folded configuration in a stomach of a patient, allowing the gastric residence system in the folded configuration to assume an open configuration.

Embodiment 54. The method of embodiment 52 or 53, wherein a thickness of the coating on the enrobed gastric residence dosage form is from 50 to 250 microns.

Embodiment 55. The method of any of embodiments 52-54, wherein enrobing a gastric residence system in a folded configuration with a coating to form an enrobed gastric residence dosage form comprises a rotary die encapsulation process.

Embodiment 56. The method of any of embodiments 52-55, wherein the coating comprises a softgel type shell material.

Embodiment 57. The method of any of embodiments 52-56, wherein the coating provides a hermetic seal.

Embodiment 58. The method of any of embodiments 52-57, comprising binding the gastric residence system in the folded configuration with a sleeve prior to enrobing.

Embodiment 59. The method of embodiment 58, wherein the sleeve comprises at least one of gelatin, hydroxypropyl methylcellulose, or pullulan.

Embodiment 60. The method of any of embodiments 52-59, comprising encapsulating the gastric residence system in the folded configuration with a capsule prior to enrobing.

Embodiment 61. The method of embodiment 60, wherein the capsule comprises at least one of gelatin, hydroxypropyl methylcellulose, or pullulan.

Embodiment 62. The method of any of embodiments 52-61, wherein the coating comprises water, a plasticizer, and a gelling agent.

Embodiment 63. The method of embodiment 62, wherein the coating comprises from 5 to 10 wt. % water.

Embodiment 64. The method of embodiment 62 or 63, wherein the plasticizer comprises one or more of glycerin or sorbitol.

Embodiment 65. The method of any of embodiments 62-64, wherein the coating comprises from 20 to 60 wt. % plasticizer.

Embodiment 66. The method of any of embodiments 62-65, wherein the gelling agent is one or more of gelatin, pullulan, hydroxypropyl methylcellulose, or potato starch.

Embodiment 67. The method of any of embodiments 62-66, wherein the coating comprises from 35 to 75 wt. % gelling agent.

Embodiment 68. The method of any of embodiments 52-67, wherein the coating comprises a polymer.

Embodiment 69. The method of embodiment 68, wherein the polymer comprises a polymethacrylate-based polymer.

Embodiment 70. The method of embodiment 68 or 69, wherein the coating comprises from 10 to 50 wt. % polymer.

Embodiment 71. The method of any of embodiments 52-70, comprising coating the enrobed gastric residence dosage form with a reverse-enteric coating.

Embodiment 72. The method of embodiment 71, wherein the reverse-enteric coating comprises a reverse-enteric polymer, an anti-tacking agent, and a plasticizer.

Embodiment 73. The method of embodiment 72, wherein the anti-tacking agent comprises at least one of talc or magnesium stearate.

Embodiment 74. The method of embodiment 72 or 73, wherein the plasticizer comprises at least one of a phthalate, a phosphate, a citrate, a tartrate, an adipate, a sebacate, a sulfonamide, a succinate, a glycolate, a glycerolate, a benzoate, a myristate, a halogenated phenyl, or a poloxamer.

Embodiment 75. The method of any of embodiments 72-74, wherein the plasticizer comprises at least one of triacetin or dibutyl sebacate.

Embodiment 76. The method of any of embodiments 72-75, wherein the reverse-enteric coating comprises a hydration aid.

Embodiment 77. The method of embodiment 76, wherein the hydration aid comprises at least one of a polyvinylpyrrolidone, a vinylpyrrolidone-vinyl acetate copolymer, a polyethylene glycol, mannitol, or hydroxypropyl methylcellulose.

Embodiment 78. The method of any of embodiments 53-77, wherein the enrobed gastric residence dosage form allows the gastric residence system in the folded configuration to assume the open configuration in at least 20 minutes when exposed to an aqueous pH 7.0 environment.

i Embodiment 79. The method of any of embodiments 53-78, wherein the enrobed gastric residence dosage form allows the gastric residence system in the folded configuration to assume the open configuration in at least 30 minutes when exposed to an aqueous pH 7.0 environment.

Embodiment 80. The method of any of embodiments 53-79, wherein the enrobed gastric residence dosage form allows the gastric residence system in the folded configuration to assume the open configuration in less than 20 minutes when exposed to an aqueous pH 3.0 environment.

Embodiment 81. The method of any of embodiments 53-80, wherein the enrobed gastric residence dosage form allows the gastric residence system in the folded configuration to assume the open configuration in less than 15 minutes when exposed to an aqueous pH 3.0 environment.

Embodiment 82. An enrobed gastric residence dosage form made using the method of any of embodiments 52-81, wherein the enrobed gastric residence dosage form is used to treat a patient.

Embodiment 83. The enrobed gastric residence dosage form of embodiment 82, wherein the patient is a human.

Embodiment 84. A coated enrobed gastric residence dosage form comprising: a coated enrobed gastric residence system; and a coating comprising a reverse-enteric polymer coating the enrobed gastric residence system, wherein $$\frac{\text{static coefficient of friction of coated enrobed gastric residence dosage form}}{\text{static coefficient of friction of uncoated enrobed gastric residence dosage form}} \leq 0.8.$$

Embodiment 85. The coated enrobed gastric residence dosage form of embodiment 84, wherein a static coefficient of friction of the coated enrobed gastric residence dosage form is less than 0.3.

Embodiment 86. The coated enrobed gastric residence dosage form of embodiment 84 or 85, wherein the static coefficient of friction of the coated enrobed gastric residence dosage form is less than 0.2.

Embodiment 87. The coated enrobed gastric residence dosage form of any of embodiments 84-86, wherein the static coefficient of friction of the coated enrobed gastric residence dosage form is less than 0.1.

Embodiment 88. The coated enrobed gastric residence dosage form of any of embodiments 84-87, wherein $$\frac{\text{static coefficient of friction of coated}}{\text{static coefficient of friction of uncoated}} \leq 0.5.$$
$$\text{enrobed gastric residence dosage form}$$

Embodiment 89. The coated enrobed gastric residence dosage form of any of embodiments 84-88, wherein the static coefficient of friction of the coated enrobed gastric residence dosage form is at least 0.08 less than that of an uncoated enrobed gastric residence dosage form.

Embodiment 90. The coated enrobed gastric residence dosage form of any of embodiments 84-89, wherein the static coefficient of friction of the coated enrobed gastric residence dosage form is at least 0.15 less than that of an uncoated enrobed gastric residence dosage form.

Embodiment 91. The coated enrobed gastric residence dosage form of any of embodiments 84-90, wherein the static coefficient of friction of the coated enrobed gastric residence dosage form is at least 0.2 less than that of an uncoated enrobed gastric residence dosage form.

Embodiment 92. The coated enrobed gastric residence dosage form of any of embodiments 84-91, wherein the reverse-enteric polymer comprises a polymethacrylate.

Embodiment 93. The coated enrobed gastric residence dosage form of any of embodiments 84-92, comprising 10 to 50 wt. % reverse-enteric polymer.

Embodiment 94. The coated enrobed gastric residence dosage form of any of embodiments 84-93, wherein the coating comprises an anti-tacking agent.

Embodiment 95. The coated enrobed gastric residence dosage form of any of embodiments 84-94, wherein the anti-tacking agent comprises at least one of talc or magnesium stearate.

Embodiment 96. The coated enrobed gastric residence dosage form of embodiment 95 or 96, comprising 5 to 30 wt. % anti-tacking agent.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Reference to "about" a value or parameter herein includes (and describes) variations that are directed to that value or parameter per se. For example, description referring to "about X" includes description of "X".

As used herein, the singular forms "a," "an," and "the" are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

This application discloses several numerical ranges in the text and figures. The numerical ranges disclosed inherently support any range or value within the disclosed numerical ranges, including the endpoints, even though a precise range limitation is not stated verbatim in the specification because this disclosure can be practiced throughout the disclosed numerical ranges.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

The invention claimed is:

1. An enrobed gastric residence dosage form comprising:
   a gastric residence system in a folded configuration; and
   a first coating enrobing the gastric residence system in the folded configuration; and
   a second coating on the first coating enrobing the gastric residence system in the folded configuration, wherein the first coating and the second coating do no comprise a therapeutic agent, and
   wherein the enrobed gastric residence dosage form is configured to release the gastric residence system in a stomach of a patient, allowing the gastric residence system to assume an open configuration.

2. The enrobed gastric residence dosage form of claim 1, wherein a thickness of the first coating enrobing the gastric residence system in the folded configuration is from 50 to 250 microns.

3. The enrobed gastric residence dosage form of claim 1, wherein the first coating enrobing the gastric residence system in the folded configuration is applied to the gastric residence system in the folded configuration using a rotary die encapsulation process.

4. The enrobed gastric residence dosage form of claim 1, wherein the first coating enrobing the gastric residence system in the folded configuration comprises a softgel type shell material.

5. The enrobed gastric residence dosage form of claim 1, wherein the first coating enrobing the gastric residence system in the folded configuration provides a hermetic seal.

6. The enrobed gastric residence dosage form of claim 1, wherein the first coating enrobing the gastric residence system in the folded configuration comprises from 5 to 10 wt. % water.

7. The enrobed gastric residence dosage form of claim 1, wherein the first coating enrobing the gastric residence system in the folded configuration comprises from 20 to 60 wt. % one or more of glycerin or sorbitol.

8. The enrobed gastric residence dosage form of claim 1, wherein the first coating enrobing the gastric residence system in the folded configuration comprises from 35 to 75 wt. % one or more of gelatin, pullulan, hydroxypropyl methylcellulose, or potato starch.

9. The enrobed gastric residence dosage form of claim 1, wherein the first coating enrobing the gastric residence system in the folded configuration comprises from 10 to 50 wt. % a polymethacrylate-based polymer.

10. The enrobed gastric residence dosage form of claim 1, comprising a sleeve, wherein the sleeve surrounds at least a portion of the gastric residence system in the folded configuration, wherein the sleeve comprises at least one of gelatin, hydroxypropyl methylcellulose, or pullulan.

11. The enrobed gastric residence dosage form of claim 1, comprising a capsule encapsulating the gastric residence system in the folded configuration, wherein the capsule comprises at least one of gelatin, hydroxypropyl methylcellulose, or pullulan.

12. The enrobed gastric residence dosage form of claim 1, wherein the second coating on the first coating enrobing the gastric residence system comprises a polymethacrylate-based polymer.

13. The enrobed gastric residence dosage form of claim 1, wherein the second coating on the first coating enrobing the gastric residence system comprises an anti-tacking agent comprising at least one of talc or magnesium stearate.

14. The enrobed gastric residence dosage form of claim 1, wherein the second coating on the first coating enrobing the gastric residence system comprises a plasticizer comprising at least one of a phthalate, a phosphate, a citrate, a tartrate, an adipate, a sebacate, a sulfonamide, a succinate, a glycolate, a glycerolate, a benzoate, a myristate, a halogenated phenyl, a poloxamer, triacetin or dibutyl sebacate.

15. The enrobed gastric residence dosage form of claim 1, wherein the second coating on the first coating enrobing the gastric residence system comprises a hydration aid comprising at least one of a polyvinylpyrrolidone, a vinylpyrrolidone-vinyl acetate copolymer, a polyethylene glycol, mannitol, or hydroxypropyl methylcellulose.

16. The enrobed gastric residence dosage form of claim 1, wherein the enrobed gastric residence dosage form allows the gastric residence system in the folded configuration to assume an open configuration in at least 20 minutes when exposed to an aqueous pH 7.0 environment.

17. The enrobed gastric residence dosage form of claim 1, wherein the enrobed gastric residence dosage form allows the gastric residence system in the folded configuration to assume an open configuration in less than 20 minutes when exposed to an aqueous pH 3.0 environment.

18. The enrobed gastric residence dosage form of claim 1, wherein the enrobed gastric residence dosage form is used to treat a human.

* * * * *